(12) United States Patent
Henderson et al.

(10) Patent No.: US 9,380,951 B2
(45) Date of Patent: Jul. 5, 2016

(54) NON-INVASIVELY MONITORING BLOOD PARAMETERS

(75) Inventors: Leslie G. Henderson, Cicero, IN (US); Theodore M. Bailey, Indianapolis, IN (US)

(73) Assignee: Covidien LP, Mansfield, MA (US)

( * ) Notice: Subject to any disclaimer, the term of this patent is extended or adjusted under 35 U.S.C. 154(b) by 1735 days.

(21) Appl. No.: 12/025,564

(22) Filed: Feb. 4, 2008

(65) Prior Publication Data

US 2008/0132769 A1 Jun. 5, 2008

Related U.S. Application Data

(63) Continuation of application No. 10/958,458, filed on Oct. 5, 2004, now Pat. No. 7,341,560.

(51) Int. Cl.
| | |
|---|---|
| *A61B 5/00* | (2006.01) |
| *A61B 5/02* | (2006.01) |
| *A61B 5/024* | (2006.01) |
| *A61B 5/021* | (2006.01) |
| *A61B 5/1455* | (2006.01) |

(52) U.S. Cl.
CPC ........... *A61B 5/02416* (2013.01); *A61B 5/0059* (2013.01); *A61B 5/021* (2013.01); *A61B 5/02125* (2013.01); *A61B 5/14551* (2013.01); *A61B 5/14552* (2013.01); *A61B 5/6814* (2013.01); *A61B 5/6826* (2013.01); *A61B 5/6838* (2013.01); *A61B 5/6824* (2013.01); *A61B 2560/0412* (2013.01)

(58) Field of Classification Search
USPC ............................ 600/324, 325, 327, 332, 513
See application file for complete search history.

(56) References Cited

U.S. PATENT DOCUMENTS 4,949,725 A * 8/1990 Raviv et al. .................... 600/544
5,020,540 A * 6/1991 Chamoun .................... 600/509
(Continued)

FOREIGN PATENT DOCUMENTS

EP 0638281 A1 2/1995
WO WO-9203966 A1 3/1992
(Continued)

OTHER PUBLICATIONS

Non-Final Office Action dated Sep. 12, 2006 from U.S. Pat. No. 7,341,560.
(Continued)

*Primary Examiner* — Etsub Berhanu

(57) ABSTRACT

An apparatus for monitoring vital sign parameters in a biological entity is disclosed. In an embodiment, the apparatus includes at least one light source for transmitting light through the biological entity and at least one photodetector for receiving light transmitted through the biological entity. At least one light source and at least one photodetector are configured to be positioned proximate the biological entity in a manner that does not significantly impede blood flow through the biological entity. A signal is generated in response to the transmittance or reflectance of light through the biological entity. The signal corresponds to at least one characteristic of the generally unimpeded blood flow through the biological entity. The apparatus also includes a control system configured to analyze the signal to determine vital sign parameters in the biological entity. A method for monitoring vital sign parameters in a biological entity is also provided.

18 Claims, 18 Drawing Sheets

(56) References Cited

U.S. PATENT DOCUMENTS

| | | | |
|---|---|---|---|
| 5,111,817 | A | 5/1992 | Clark et al. |
| 5,148,812 | A * | 9/1992 | Verrier et al. ............... 600/517 |
| 5,247,931 | A | 9/1993 | Norwood |
| 5,379,774 | A | 1/1995 | Nishimura et al. |
| 5,676,139 | A | 10/1997 | Goldberger et al. |
| 5,836,887 | A * | 11/1998 | Oka et al. ..................... 600/494 |
| 6,050,951 | A * | 4/2000 | Friedman et al. ............. 600/485 |
| 6,178,343 | B1 * | 1/2001 | Bindszus et al. .............. 600/323 |
| 6,298,267 | B1 * | 10/2001 | Rosborough et al. ............ 607/6 |
| 6,470,893 | B1 | 10/2002 | Boesen |
| 6,584,335 | B1 * | 6/2003 | Haar et al. .................... 600/322 |
| 6,648,820 | B1 * | 11/2003 | Sarel ............................ 600/300 |
| 2002/0038081 | A1 * | 3/2002 | Fein ................ A61B 5/14552 600/323 |
| 2003/0036690 | A1 | 2/2003 | Geddes et al. |
| 2003/0181798 | A1 * | 9/2003 | Al-Ali ........................... 600/324 |
| 2004/0059209 | A1 * | 3/2004 | Al-Ali et al. .................. 600/323 |
| 2004/0087846 | A1 * | 5/2004 | Wasserman .................... 600/323 |
| 2004/0249299 | A1 * | 12/2004 | Cobb ............................ 600/529 |
| 2004/0249302 | A1 * | 12/2004 | Donoghue et al. ............ 600/544 |
| 2005/0106977 | A1 * | 5/2005 | Coulston ....................... 442/301 |

FOREIGN PATENT DOCUMENTS

| | | |
|---|---|---|
| WO | WO-9518564 A1 | 7/1995 |
| WO | WO 03092491 A1 * | 11/2003 |

OTHER PUBLICATIONS

Final Office Action dated Jun. 13, 2007 from U.S. Pat. No. 7,341,560.

Extended European Search Report from PCT/US2005035520 (5 pages).

* cited by examiner

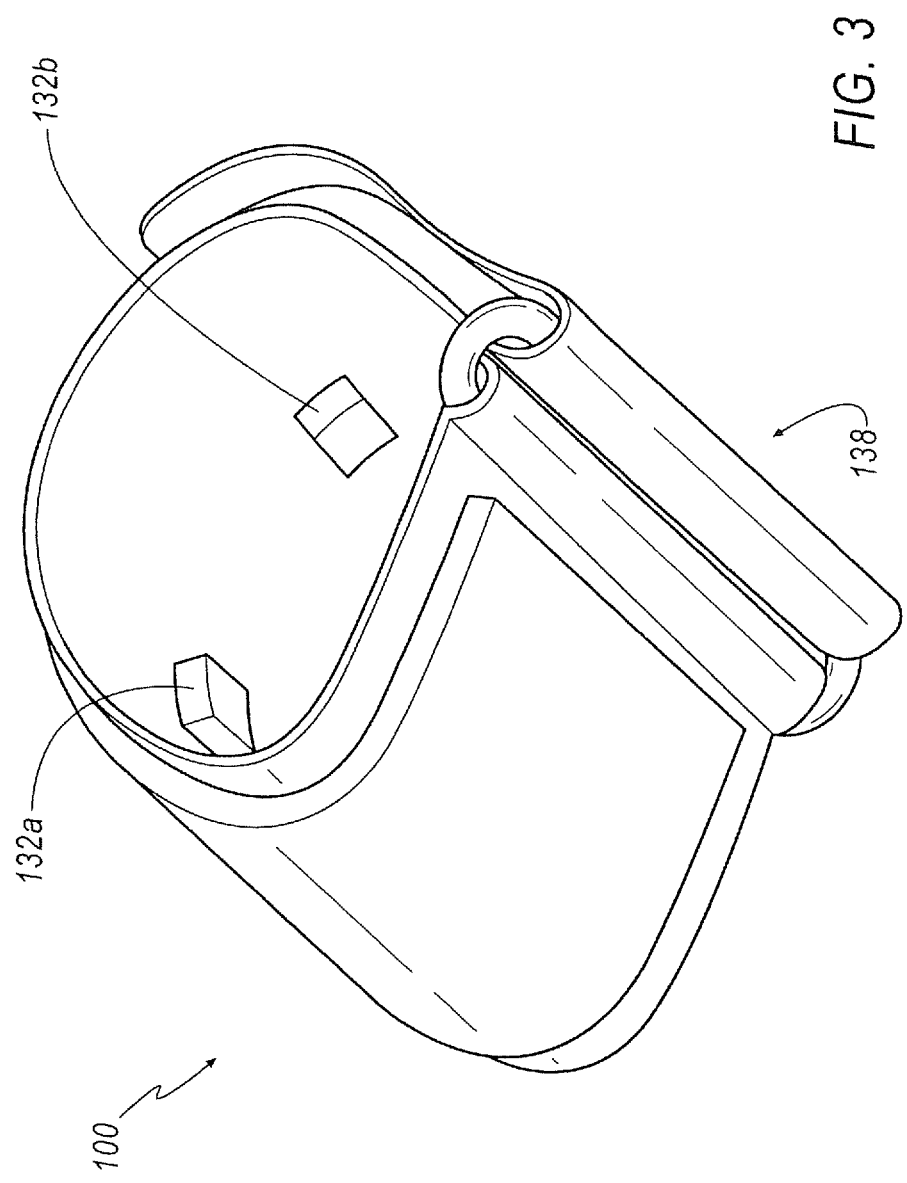

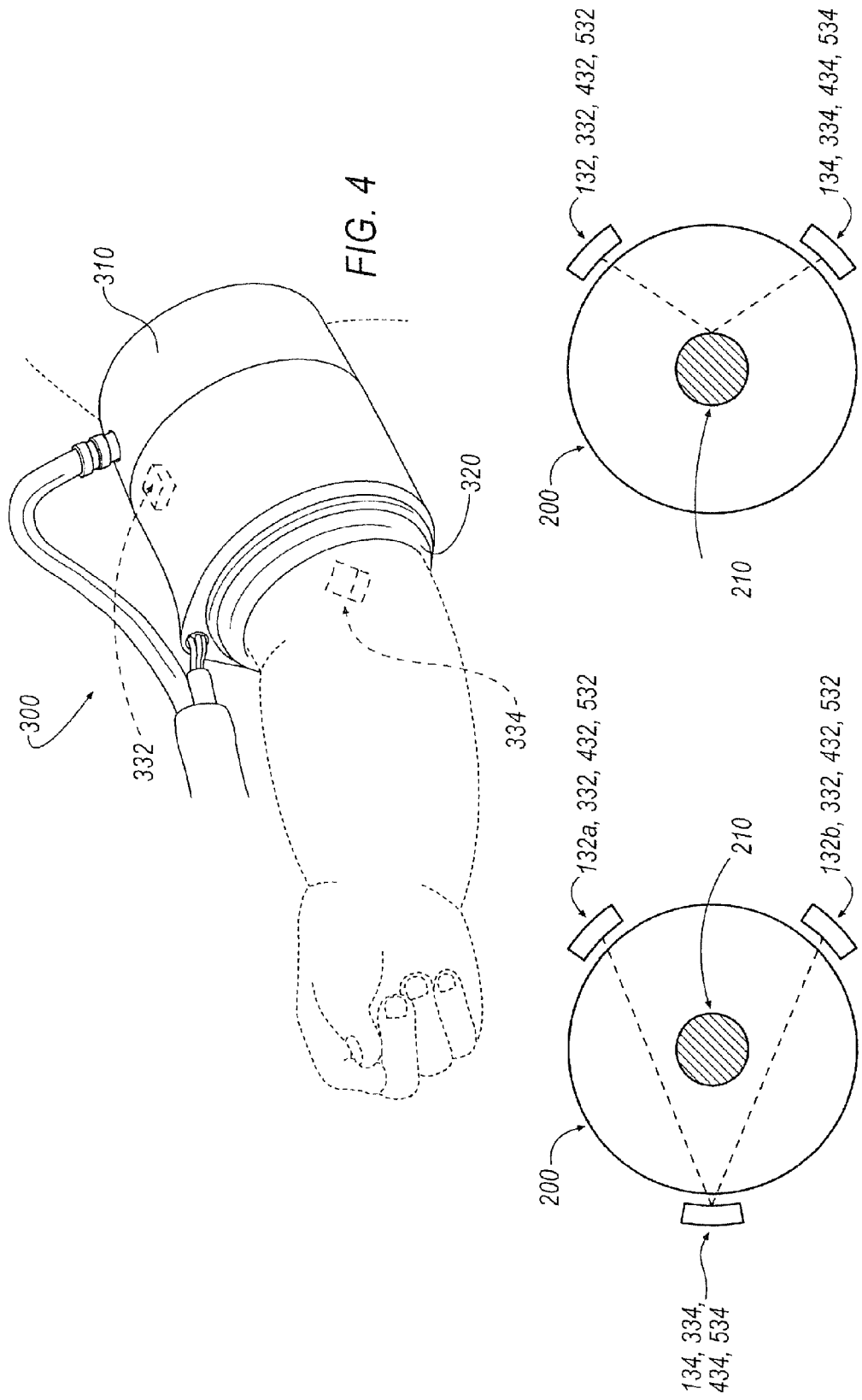

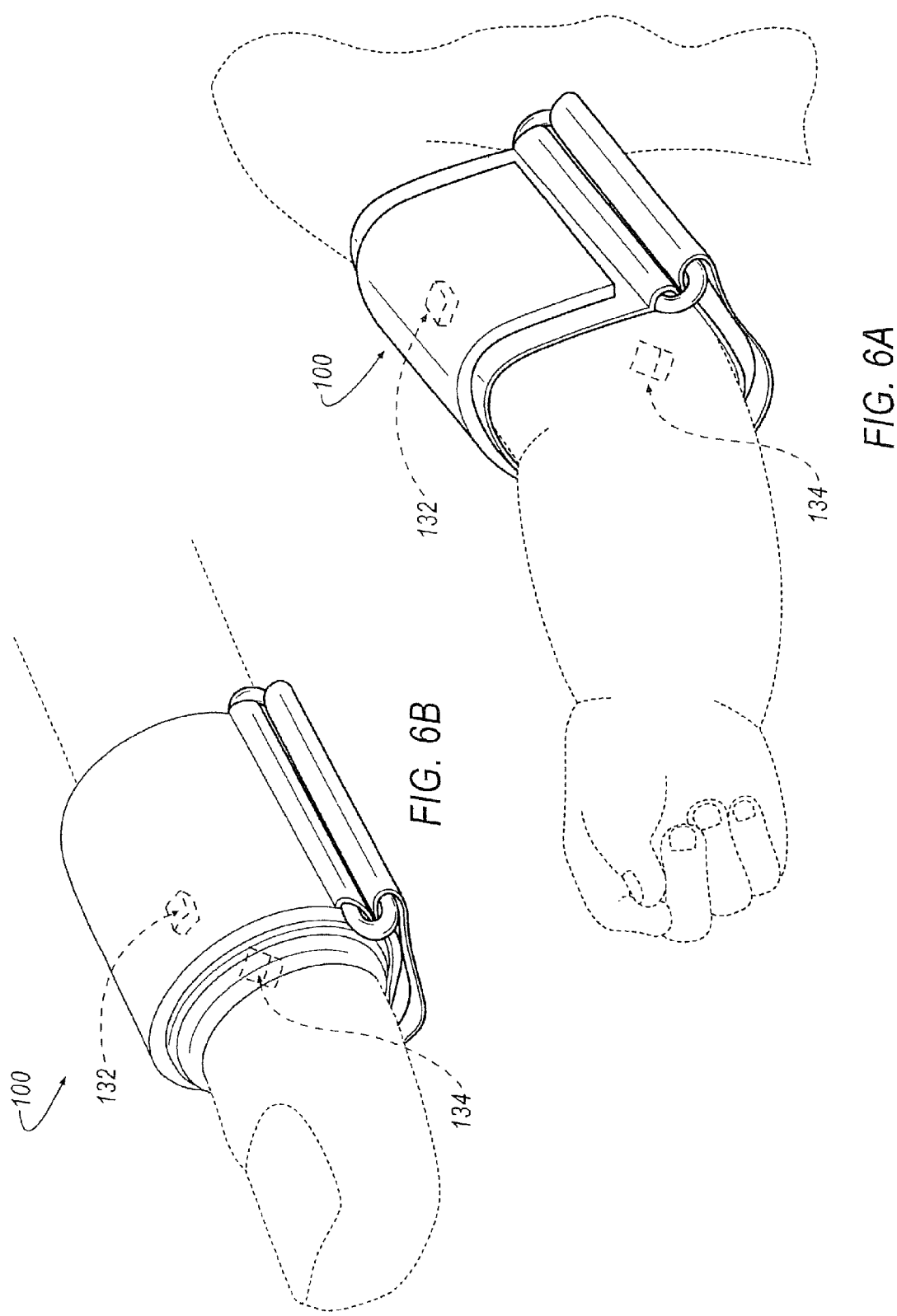

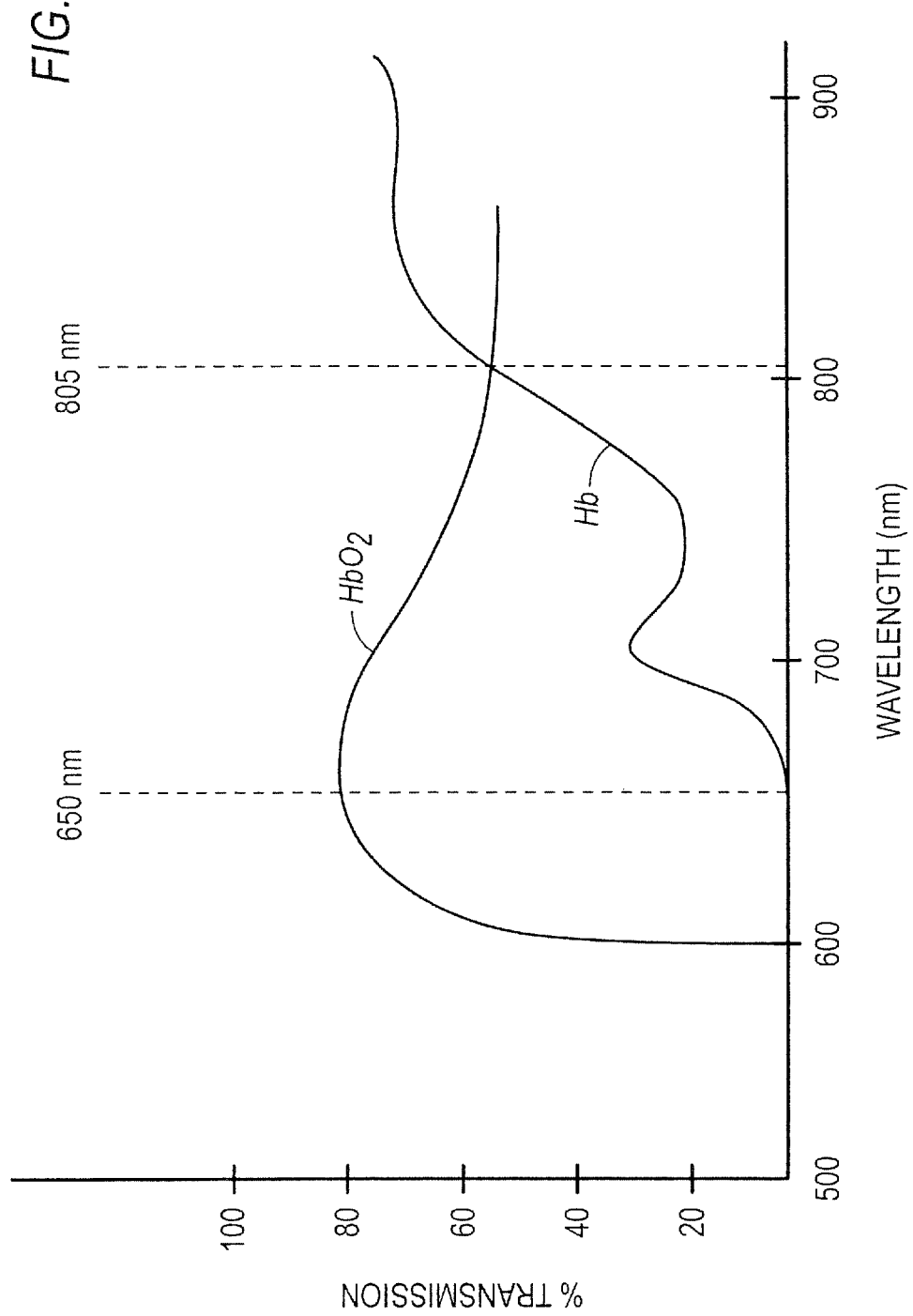

NON-INVASIVELY MONITORING BLOOD PARAMETERS

This application is a continuation of U.S. application Ser. No. 10/958,458, filed Oct. 5, 2004, entitled APPARATUSES AND METHODS FOR NON-INVASIVELY MONITORING BLOOD PARAMETERS, which application is hereby incorporated herein by reference in its entirety.

The present invention relates to medical devices and, more particularly, to apparatuses and methods for non-invasively monitoring vital sign parameters of a biological entity, such as a neonate.

BACKGROUND OF THE INVENTION

A basic requirement in determining the health of a human adult or neonate is to measure certain vital sign parameters, such as blood pressure, pulse rate, blood oxygen saturation, and respiratory rate. For example, measuring blood pressure in a human adult is typically accomplished using either an oscillometric-based method or an auscultatory method, both of which traditionally involve the application of an inflatable blood pressure cuff around the arm of the subject. While oscillometric-based and auscultatory methods are easily implemented with a human adult, these methods are not well suited for subjects such as neonates due to their diminutive size and inability to comprehend and cooperate with the procedure.

Beyond the inability to accurately monitor vital sign parameters in a small subject, traditional methods of measuring vital sign parameters are generally carried out on a periodic basis, as opposed to providing near-continuous monitoring. This is because traditional methods of monitoring generally required that the subject be disturbed in some manner. For example, in monitoring blood pressure, blood flow through the subject's body member was occluded, through inflation of the blood pressure cuff, in order to measure blood pressure. Inflation of the blood pressure cuff may be disturbing to a neonate, particularly during their rest if performed on a periodic basis.

Accordingly, a need exists for apparatuses and methods for monitoring vital sign parameters, such as blood pressure, oxygen saturation, pulse rate, and respiration, regardless of whether the subject is a human adult, a neonate or some other biological entity. The apparatuses and methods should be easily implemented and obtain accurate results, as well as be carried out in a near-continuous manner so as to allow for monitoring without disturbing the subject. Also, the apparatuses and methods should be employed such that any biological entity, regardless of size, may be monitored.

SUMMARY OF THE INVENTION

The present invention provides apparatuses for monitoring vital sign parameters of a biological entity. In one embodiment of the invention, the apparatuses include at least one light source for transmitting light through the biological entity and at least one photodetector for receiving light transmitted through the biological member. At least one light source and at least one photodetector are configured to be positioned proximate the biological entity in a manner that does not significantly impede blood flow through the biological entity. A signal is generated in response to the transmittance or reflectance of light through the biological entity. The signal corresponds to at least one characteristic of the generally unimpeded blood flow through the biological member. The apparatuses also include a control system configured to analyze the signal to determine blood pressure, oxygen saturation, pulse rate, perfusion index, cardiac index, vascular elasticity. and respiration, among other blood parameters, of the biological entity.

The present invention also provides methods for monitoring vital sign parameters in a biological entity. In one embodiment, the method includes positioning at least one sensor assembly proximate the biological entity. A signal is generated by at least one sensor assembly that corresponds to at least one characteristic of the blood flow through the biological entity. The signal is analyzed to determine blood pressure, oxygen saturation, pulse rate, perfusion index, cardiac index, vascular elasticity, and respiration, among other blood parameters, of the biological entity.

DESCRIPTION OF THE DRAWINGS

Embodiments of the invention will now be described, by way of example, with reference to the accompanying drawings, wherein:

FIG. 3 is a depiction of the trans-illuminating cuff of FIG. 1A from a third perspective;

FIG. 4 is a perspective view of a trans-illuminating cuff according to another embodiment of the invention;

FIGS. 5A and 5B depict two possible optical paths that may be established through a biological member;

FIG. 6A is a perspective view of the trans-illuminating cuff of FIG. 1A applied to the arm of a neonate;

FIG. 6B is a perspective view of the trans-illuminating cuff of FIG. 1A applied to the finger of an adult;

FIG. 14 is a graph that illustrates the spectral characteristics of hemoglobin (Hb) and oxygenated hemoglobin (HbO2);

DETAILED DESCRIPTION OF THE INVENTION

Figure 1:
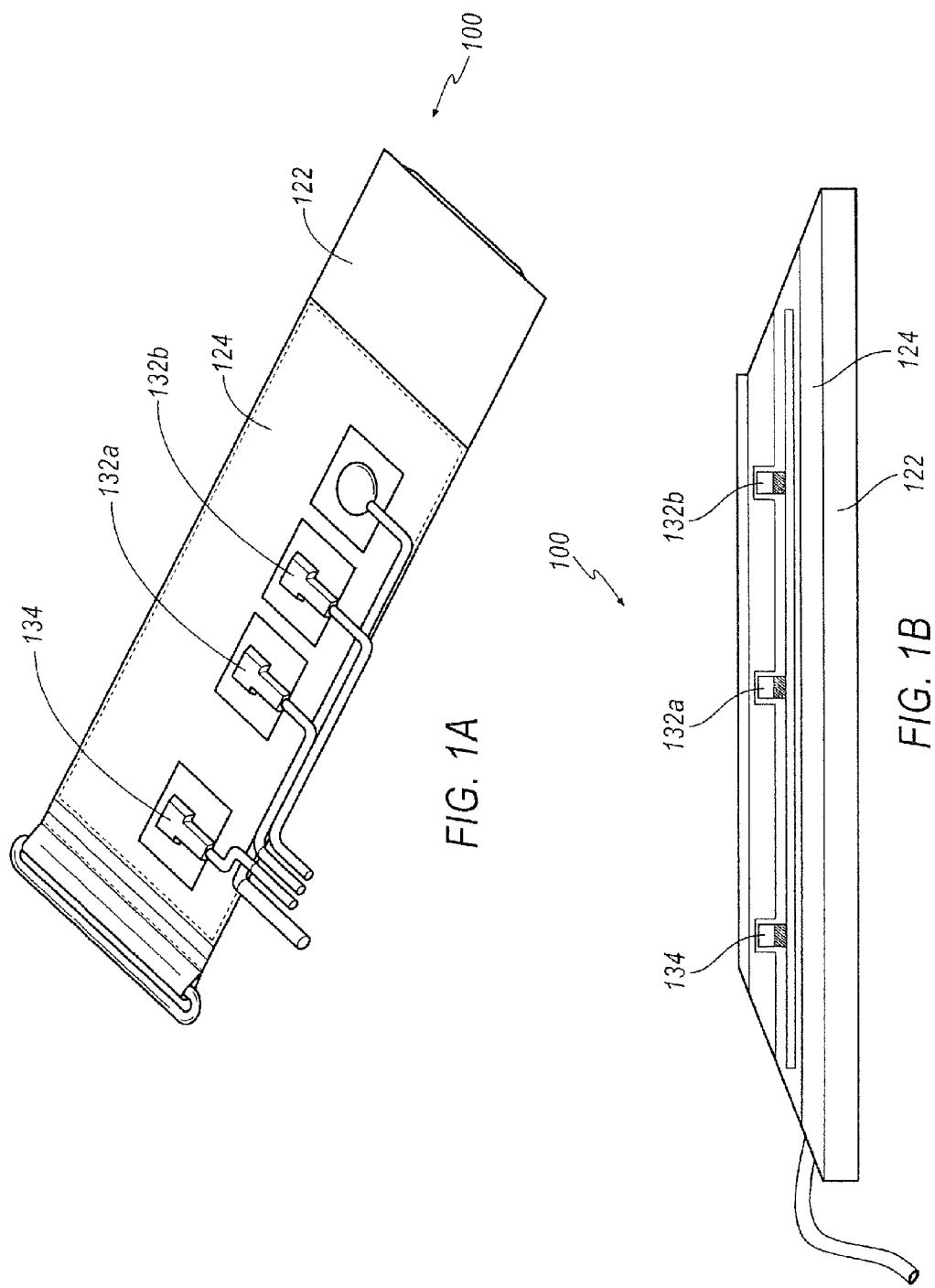
FIG. 1A depicts, from a first perspective, a trans-illuminating cuff according to an embodiment of the invention.
FIG. 1B is a cross-sectional view of the trans-illuminating cuff of FIG. 1A.

One embodiment of the present invention will now be described with reference to FIGS. 1-3. Illustrated in FIG. 1A is one side of a member trans-illuminating cuff 100 for monitoring certain vital sign parameters of a biological entity. A particular biological entity that is discussed in the several embodiments is a newborn, neonate, or infant (collectively referred to as "neonate" for the remainder of the application and understood to represent not only a person in their early stages of life, but any person of relatively diminutive size, such as an infant, regardless of age). Although the following describes these several embodiments in use with a neonate, it must be understood that these embodiments may also be used to monitor the vital signs of other biological entities such as an adult person or animals (e.g., canines and primates).

In the illustrated embodiment, cuff 100 includes a flexible support member 122 that can be readily wrapped or applied around an arm, leg, finger or other appendage (collectively referred to as a "limb" for the remainder of the application) of a biological entity. Incorporated within or mounted upon one side of cuff 100 is at least one light source 132 and at least one photodetector 134 positioned to diametrically oppose light source 132 when cuff 100 is applied over a limb of a neonate. One suitable type of light source for use in cuff 100 is a light emitting diode (LED), such as the type L660/805/975-40D00, available from Epitex, Kyoto, Japan, and a suitable photodetector is a photoresistor or photodiode, such as the QSD723 photoresistor available from QT Optoelectronics. However, other light sources and photodetectors for generating and receiving one or more frequencies of light may also be used in cuff 100 without departing from the spirit and scope of the invention.

Figure 2:
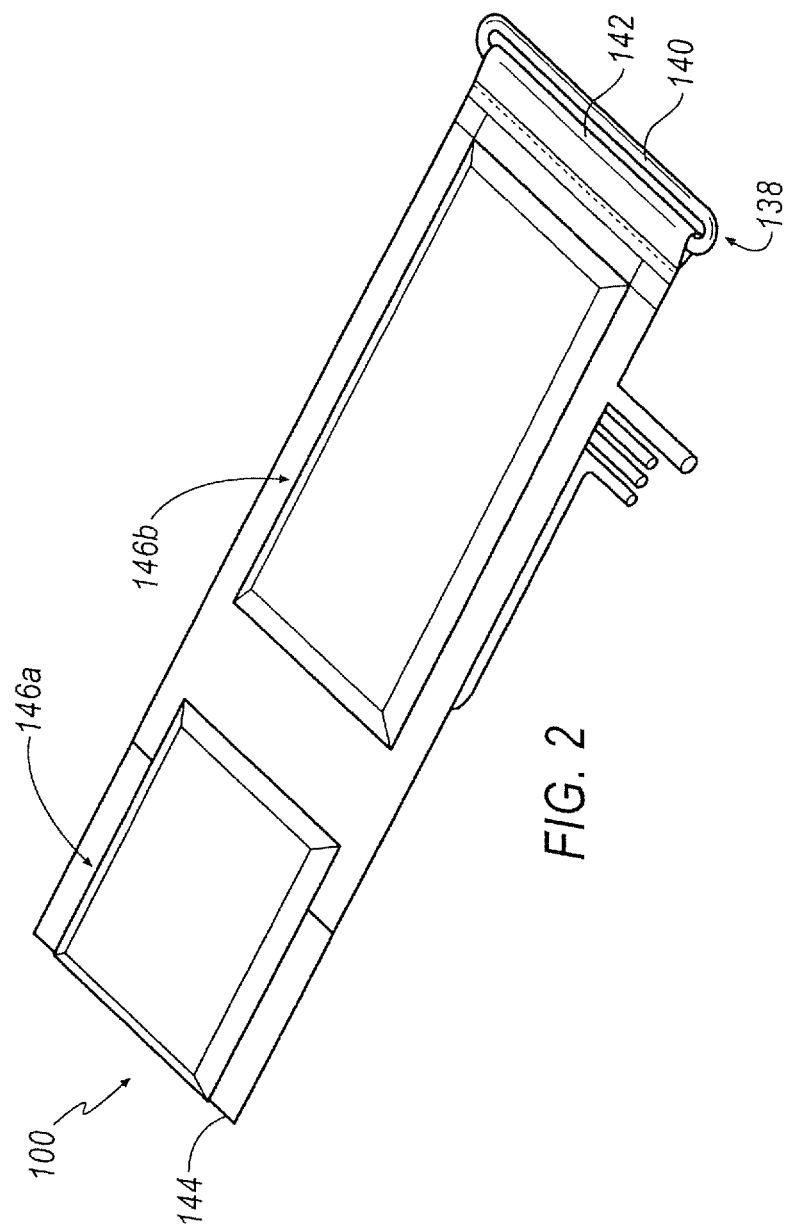
FIG. 2 is a view of the trans-illuminating cuff of FIG. 1A from a second perspective.

In the embodiment illustrated in FIGS. 1-3, cuff 100 includes two light sources 132a and 132b that are spaced along the interior side of cuff 100 so as to oppose photodetector 134 when cuff 100 is applied over a limb 200 (see, e.g., FIG. 5A). This dual light source configuration provides for increased transmission of light through the tissue bed and around a bone 210 of limb 200. Alternatively, light source 132 and photodetector 134 may be positioned side-by-side to allow for the monitoring of blood parameters based not on light transmitted directly from the light source 132 to the photodetector 134, but instead on light transmitted into the tissue of the limb 200 by light source 132 and subsequently reflected back to photodetector 134 (see, e.g., FIG. 5B).

As illustrated in FIG. 2, cuff 100 also includes an attachment device 138 for securing cuff 100 to limb 200 of a neonate. According to the present embodiment, attachment device 138 includes a cinch-loop 140 attached to a first end 142 of the flexible support member 122 through which a second end 144 extends when cuff 100 is applied to the limb of a neonate. In the illustrated configuration, hook-and-loop style fastener components 146a and 146b, such as Velcro, are applied to the second, or exterior, side of flexible support member 122. Once cuff 100 is applied to limb 200 of a neonate, fastener components 146a and 146b may be used to secure the cuff 100 in its wrapped position without significantly impeding the flow of blood through the limb (see, e.g., FIGS. 6A and 6B). In an alternative embodiment, cuff 100 may lack a cinch-loop 140, relying entirely on hook-and-loop style fastener components 146a and 146b to secure cuff 100. In addition, further embodiments may forgo the hook-and-loop style fastener components 146a and 146b in favor of other attachment means, such as, for instance, adhesives, reusable or otherwise, and other types of variable tension fastening systems.

In addition to light source 132 and photodetector 134, cuff 100 may optionally include one or more inflatable bladders 124 that are either incorporated into cuff 100 or mounted to an interior side of cuff 100. Upon placing cuff 100 around limb 200 of a neonate, bladder 124 may be inflated to a relatively low pressure level that would aid in securing cuff 100 in position while not significantly impeding the flow of blood through limb 200. Alternatively, as will be discussed later, it may be desirable to include a bladder 124 that may be inflated to a sufficiently high enough pressure level to temporarily obstruct the flow of blood through limb 200.

Regardless of either of the above intended functions, the addition of a bladder 124 to cuff 100 may be done in such a manner as to ensure that light source 132 and photodetector 134 optically communicate with limb 200. For illustrative purposes, consider the following two embodiments. In a first embodiment, bladder 124 mounts to an interior side of cuff 100 over light source 132 and photodetector 134. To ensure that neither light source 132 nor photodetector 134 are obstructed, bladder 124 may be fashioned from a material, such as polyurethane, which is optically transparent to the wavelength of light emitted by light source 132 and to which photodetector 134 is sensitive. Alternatively, according to another embodiment, cuff 100 may incorporate a bladder 124 in such a manner that when bladder 124 is inflated, light source 132 and photodetector 134 remain in contact with or proximal to limb 200. This can be accomplished, for example, by configuring cuff 100 so that light source 132 and photodetector 134 are mounted not upon flexible support member 122, but upon bladder 124.

According to another embodiment of the invention, flexible support member 122 may include a generally cylindrical sleeve (not illustrated) that may be slipped around the limb 200 of a neonate. To accommodate limbs 200 of different sizes, the generally cylindrical sleeve may possess elastic characteristics that allow it to stretch and contract as a limb 200 is inserted into the sleeve. The contractile forces generated by the sleeve as it is slipped around a limb 200 also serve to secure the placement of the sleeve without significantly impeding blood flow through the limb.

In still another embodiment of the invention, flexible support member 122 may include a generally cylindrical sleeve that does not have elastic characteristics. Instead, at least one bladder 124 may be incorporated into the sleeve or mounted upon the interior surface of the sleeve. Once sleeve is slipped around the limb 200 of a neonate, bladder 124 may be inflated with sufficient pressure to secure the sleeve around the limb without significantly impeding blood flow. If desired, the bladder may also be inflated to a pressure exceeding the systolic blood pressure of the subject, thereby substantially obstructing the flow of blood through limb 200.

According to yet another embodiment of the invention, an example of which is illustrated in FIG. 4, a trans-illuminating cuff 300 is provided that includes a rigid or semis rigid housing 310, such as a plastic tube, into which limb 200 of the neonate can be inserted. Similar to the previous embodiments, at least one light source 332 and at least one photodetector 334 are incorporated into or mounted upon housing 310 in such a manner that, upon insertion of limb 200, light source 332 may transmit light through the tissue of limb 200, with the transmitted light subsequently being received by photodetector 334.

To ensure an adequate fit with different limb sizes, a resilient sleeve or layer of material 320 may be incorporated with, or mounted onto, the interior surface of housing 310. Resilient layer 320 may include, for example, foam rubber and other materials that readily compress upon being pressed against limb 200. In this manner, a fixed diameter housing 310 may accommodate various limb sizes, the resilient layer 320 compressing and expanding as needed to generally conform to the shape of limb 200. As will be appreciated, resilient layer 320 may be configured so that it does not obstruct the transmission of light from light source 332 into the tissue of limb 200, nor interfere with the reception of light by photodetector 334. This can be accomplished through selective placement of resilient layer 320 or, alternatively, by making resilient layer 320 out of a material that is optically transparent to the wavelength(s) of light transmitted by light source 332 and received by photodetector 334. In another configuration, light source 332 and photodetector 334 may be positioned on resilient layer 320 instead of housing 310. In this manner, resilient layer 320 aids in positioning the light source 332 and photodetector 334 in close proximity to limb 200 as layer 320 expands and contracts in response to the presence of limb 200.

In another configuration, housing 310 of cuff 300 may be configured so that resilient layer 320 is supplemented or replaced by at least one bladder (see, e.g., bladder 124) that are selectively inflatable to a pressure level sufficient to hold housing 310 in place on limb 200 without significantly impeding the flow of blood through limb 200. For reasons that will be described below, the bladder(s) may also be selectively inflated to a pressure exceeding the systolic blood pressure of the neonate, thereby substantially obstructing the flow of blood through limb 200.

Figure 7:
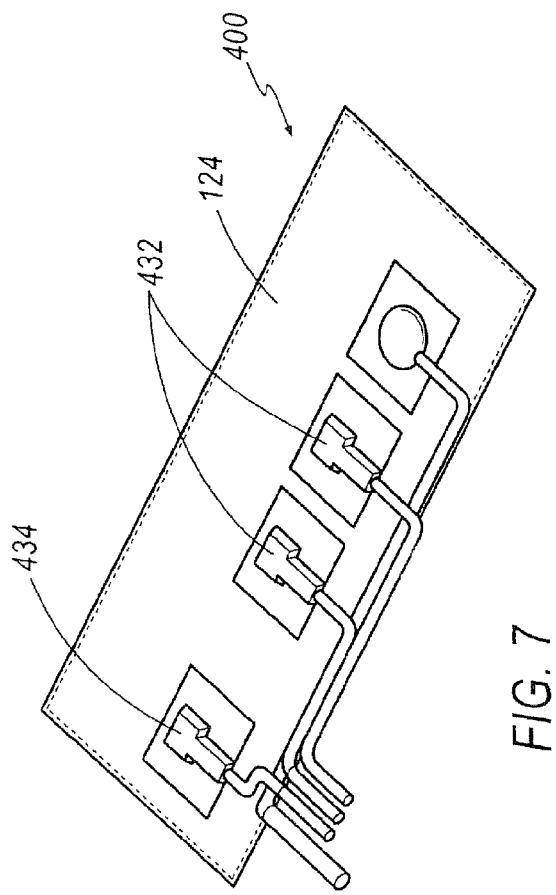
FIG. 7 depicts, from a first perspective, a trans-illuminating patch according to another embodiment of the invention.
Figure 8:
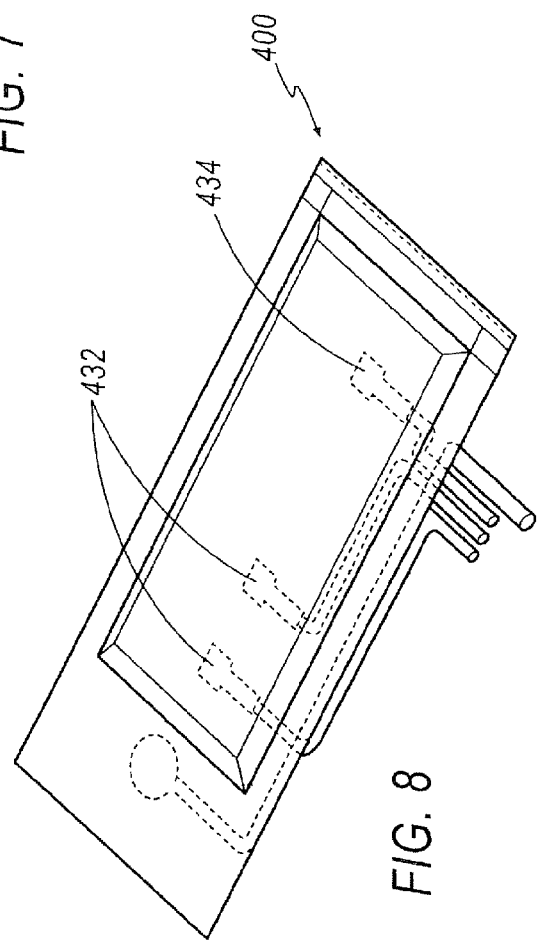
FIG. 8 is a view of the trans-illuminating patch of FIG. 7 from a second perspective.

According to another embodiment of the invention, an example of which is illustrated in FIGS. 7 and 8, a trans-illuminating patch 400 is provided. Similar to previous embodiments, at least one light source 432 and at least one photodetector 434 are incorporated into or mounted upon patch 400. Unlike the previous embodiments, patch 400 may be placed on any location or position of the neonate's body and used to monitor the vital sign parameters. Limb 200 may be used for placement, but is not required. Patch 400 may be positioned on the neonate's head, chest, neck, thigh, or other suitable location to monitor vital sign parameters (see e.g., FIG. 9, patch 400 is positioned on the head and neck of an adult person). Patch 400 may be attached to the particular area of the body with adhesives, reusable or otherwise, or some other attachment device such as a bandage, headband, or the like.

Patch 400 may be positioned on the neonate in relatively flat locations rather than encircling limb 200 like cuffs 100, 300. Therefore, light source 432 and photodetector 434 may be positioned side-by-side to allow for monitoring of vital sign parameters based not on light transmitted directly from the light source 432 to photodetector 434, but instead on light transmitted into the tissue of the neonate's body by light source 432 and subsequently reflected back to photodetector 434 (see, e.g., FIG. 5B).

In addition to light sources 432 and photodetector 434, patch 400 may also include one or more inflatable bladders (see, e.g., bladder 124) that are incorporated into patch 400. The bladders may be mounted to patch 400 such that the bladders may be between the neonate and the patch 400. In this case, the bladders may be fashioned from a material, such as polyurethane, which is optically transparent to the wavelength of light emitted by light sources 432 and to which photodetector 434 is sensitive. As will be discussed later, the bladders may be selectively inflated to a pressure exceeding the systolic blood pressure of the neonate, thereby substantially obstructing the flow of blood through that particular area of the neonate's body.

Figure 9:
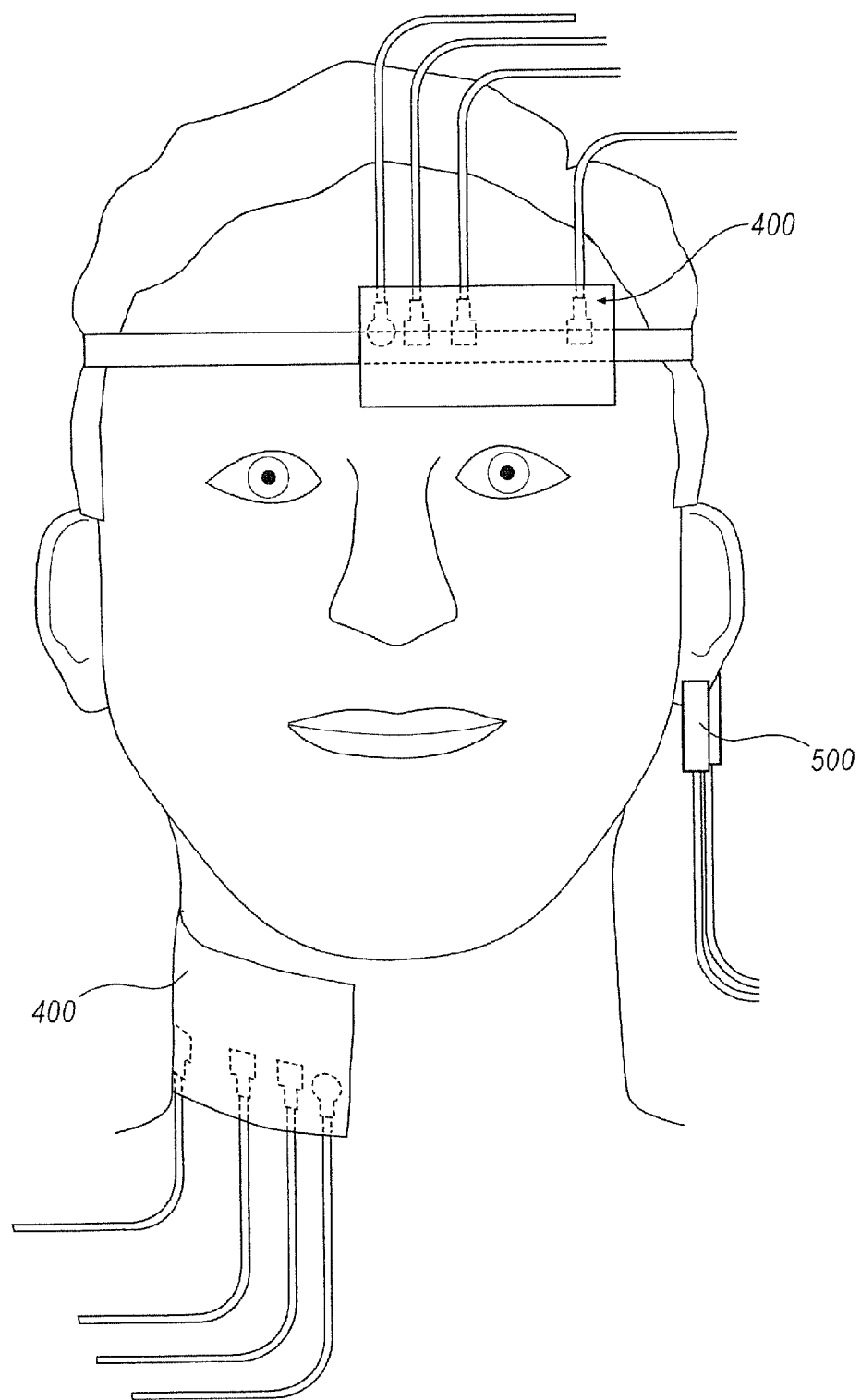
FIG. 9 is a front elevational view of the trans-illuminating patch of FIG. 7 applied to the head and neck of an adult.
Figure 10:
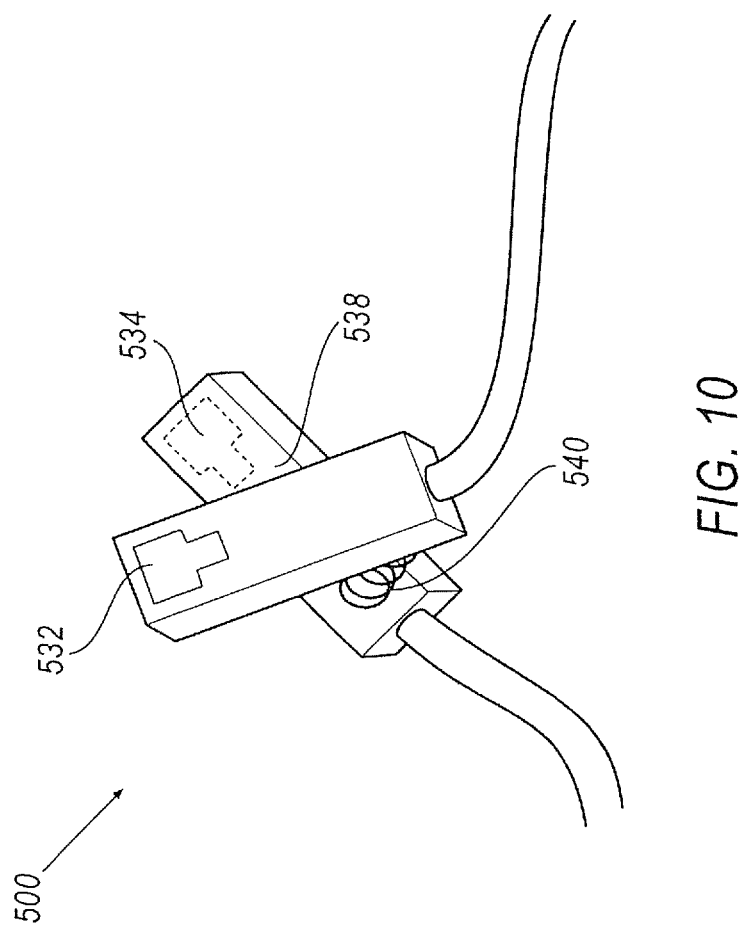
FIG. 10 is a perspective view of a trans-illuminating clip according to another embodiment of the invention.

According to another embodiment of the invention, an example of which is illustrated in FIG. 10, a trans-illuminating clip 500 is provided. Similar to previous embodiments, at least one light source 532 and at least one photodetector 534 are incorporated into or mounted upon clip 500. Clip 500 may be secured to smaller portions of the body such as earlobes, fingers, toes, and the like, and used to monitor the vital sign parameters. (see e.g., FIG. 9, clip 500 is positioned on the earlobe of an adult person). Clip 500 includes an attachment device 538 that includes a biasing member 540 such as a spring, resilient rubber, or the like, to ensure that light source 532 and photodetector 534 remain proximate the tissue of the neonate.

Figure 11:
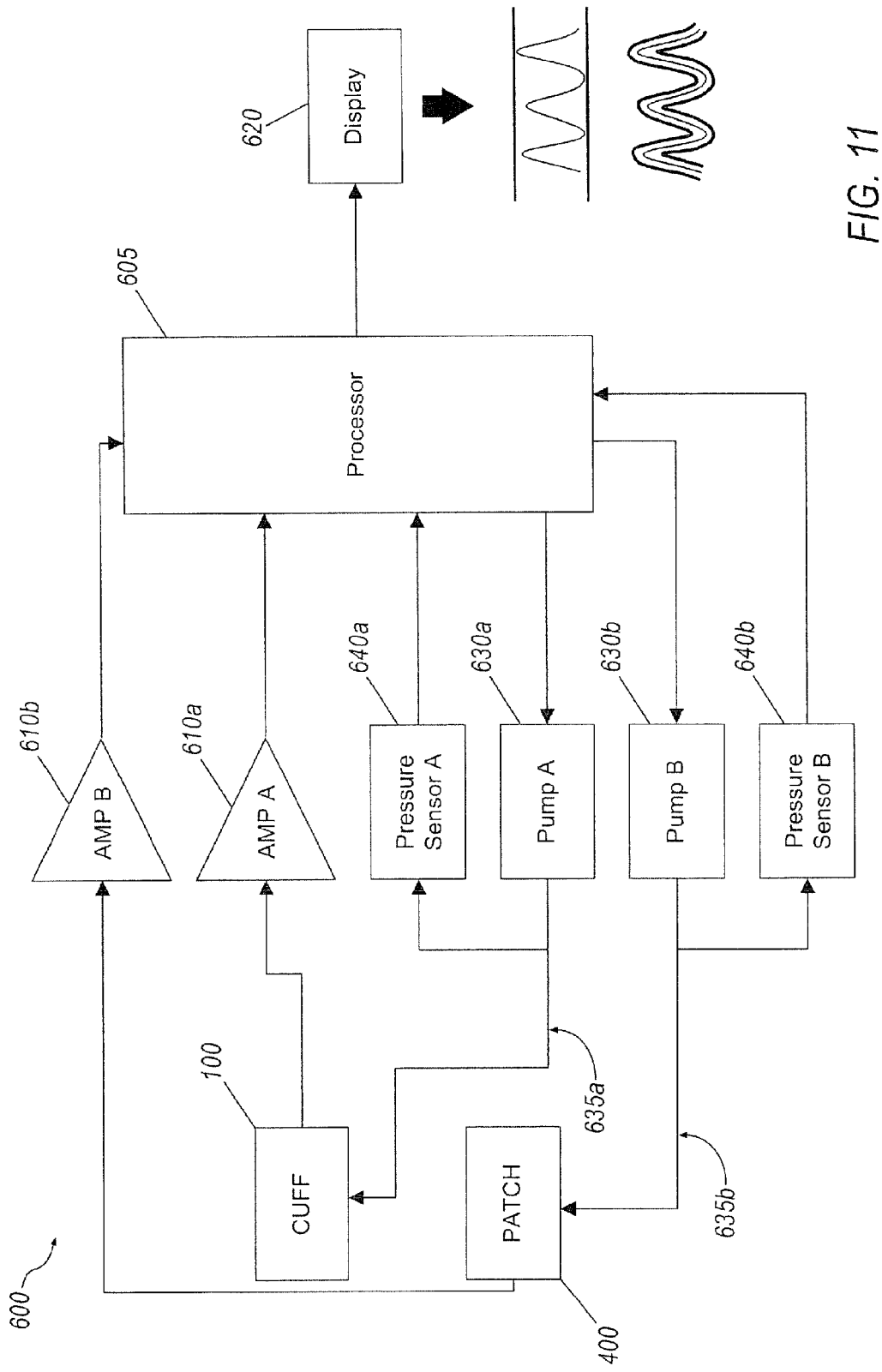
FIG. 11 is a block diagram of a vital sign parameter control system incorporating the trans-illuminating cuff of FIG. 1A and the trans-illuminating patch of FIG. 7.

With reference now to FIG. 11, a control system 600 of the present invention is shown. In an embodiment, control system 600 includes a processor 605 that controls, among other things, operation of light sources (e.g., 132, 432) and photodetectors (e.g., 134, 434) in a sensor assembly (e.g. cuff 100, patch 400). Although the sensor assembly employing light sources and photodetectors is the preferred means of generating a signal relating to vital sign parameters, it must be understood that equivalent means for generating signals relating to vital sign parameters may be employed such as ultrasound or the like. Although control system 600 is discussed controlling two sensor assemblies, it should be understood that control system 600 may control multiple channels so that multiple sensor assemblies, that are positioned on a neonate, may be used in monitoring vital sign parameters.

During vital sign parameter measurements, for example, in the measuring of blood pressure, the microprocessor energizes the light sources continually. When activated, photodetectors convert the light transmitted through the tissue in limb 200 or reflected in head 450 (or other part of the body such as the neck, chest, or thigh) into a corresponding electronic signal. This electronic signal is subsequently supplied to processor 605 for analysis after being optionally passed through amplifiers 610a and 610b. The amplified photodetector output signal is converted to digital form in the microprocessor itself if the microprocessor has an internal A/D converter, or in a separate A/D converter provided between the amplifier and the microprocessor. Results of the analysis may then be directed to a variety of output devices, such as, for example, a display screen 620. In the embodiment illustrated in FIG. 11, processor 605 is depicted as being separate from the sensor assemblies. However, in an alternative embodiment, control system 600 may be more integrated into the sensor assemblies, with one or more of the components, including processor 605, being incorporated into the sensor assemblies.

The sensor assemblies may also communicate with pumps 630a, 630b if one or more inflatable bladders are included in the sensor assemblies. Inflation and deflation of the bladders may be readily controlled by pumps 630a, 630b. For example, according to one embodiment, pumps 630a, 630b are controlled by processor 605 and convey air into the inflatable bladders through inflation tubes 635a and 635b. Pressure transducers 640a and 640b may also be incorporated into control system 600 for monitoring the pressure in inflation tubes 635a and 635b and the bladders, and conveying signals indicative of such pressure back to the processor 605. Suitable transducers are available from Cobe Labs, Littleton, Colo.

Operation of the sensor assemblies in conjunction with control system 600 to monitor certain vital sign parameters of a neonate, will now be discussed with reference to FIG. 12A. Before any vital signs may be monitored, a first sensor assembly (e.g., cuff 100) is secured around limb 200 of a neonate (see, e.g., FIG. 6A) and a second sensor assembly (e.g., patch 400) is secured to the head of a neonate (see, e.g., FIG. 9). Once appropriately positioned, control system 600 activates the sensor assemblies by operating or energizing light sources (e.g., 132, 432) and photodetectors (e.g., 134, 434). Once energized, the light sources begin to transmit light of a first wavelength or frequency. This transmitted light, representing an optical signal, passes through the skin and into the tissue of limb 200 (see, e.g., FIG. 5A) and passes through the skin and is reflected off the skull in head 450 (see, e.g., FIG. 5B). The optical signal continues to travel through the tissue making up limb 200 and head 450, including, for example, various types of skin tissue, muscle, and blood vessels. As the optical signal travels through these various constituent tissues comprising limb 200 and head 450, portions of the signal are deflected or absorbed. The remainder of the optical signal that makes it through the tissue of limb 200 is received by the photodetector. The remainder of the optical signal that is reflected through the tissue of head 450 is received by the photodetector. The photodetectors subsequently convert the optical signals into electric signals to be sent to control system 600.

At any specific point in time, this electric signal produced by the photodetectors represents the transmittance (T) of the optical signal through the tissue of limb 200 and the reflectance (R) through the tissue of head 450 at that moment in time. This transmittance (T) or reflectance (R) of the optical signal is not constant, but continuously fluctuates due to ongoing changes occurring in the tissue of limb 200 and head 450, including without limitation, changes in blood flow. Specifically, blood is distributed throughout limb 200 and head 450 by a variety of blood vessels, including, for example, arteries and arterioles. The rate and volume of blood flow through these vessels is largely dependent on blood pressure levels, which in turn are dependent on the pumping action of the heart as well as the blood vessels themselves, some of which constrict or dilate depending on the current biological state of the subject. Accordingly, the transmittance (T) of the optical signals through the tissue of limb 200 and reflectance (R) of the optical signals through the tissue of the head 450 are dependent on volumetric changes in blood flow, which, in turn, are dependent on blood pressure levels. Consequently, analysis of the electric signals, which represent variations in transmittance (T) or reflectance (R) of the optical signals due to volumetric changes in blood flow, permits the determination of several vital sign parameters, including without limitation, blood pressure oxygen saturation, pulse rate, perfusion index, cardiac index, vascular elasticity, and respiration.

Figure 12A:
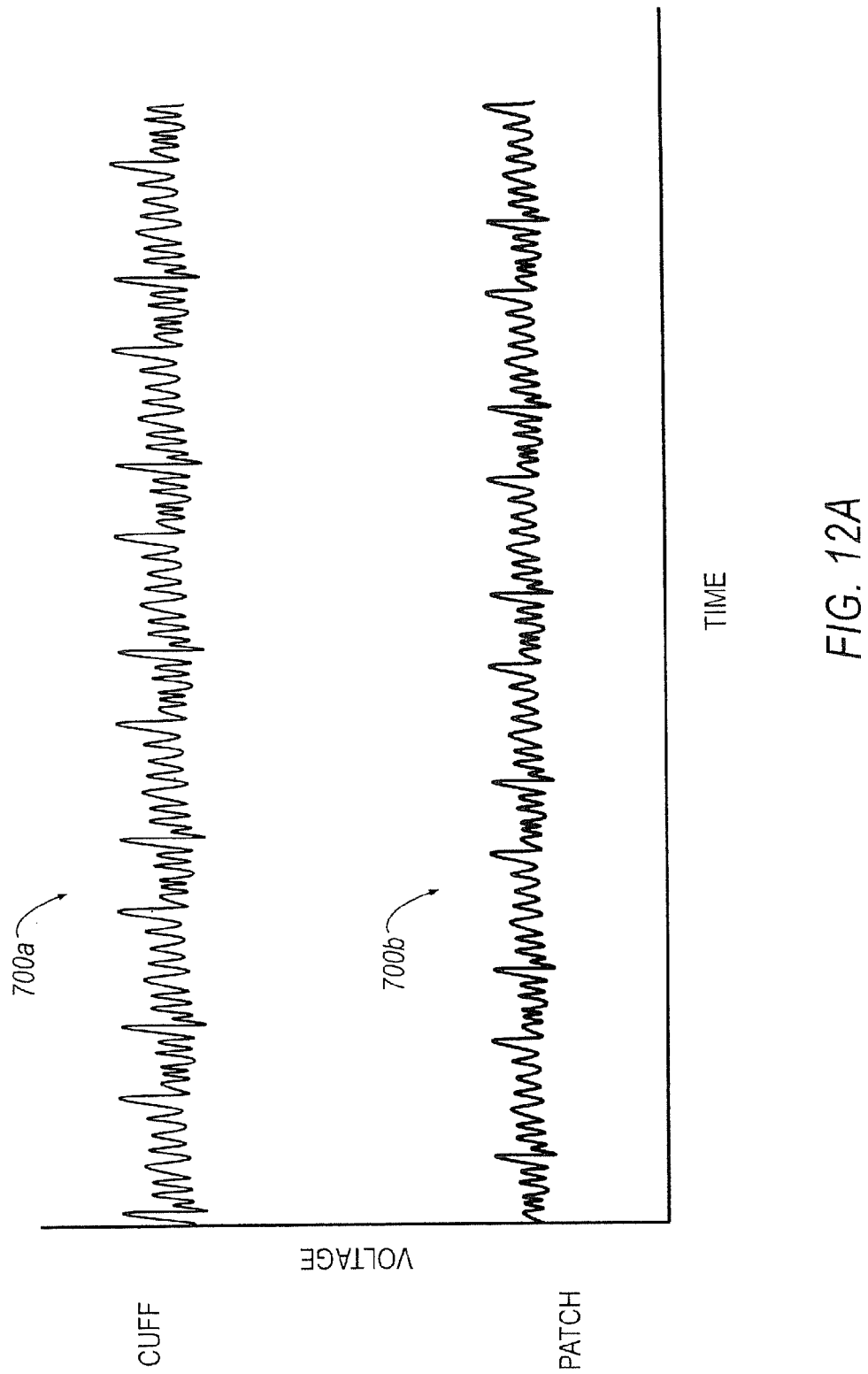
FIG. 12A are exemplary pulse waveform signals obtained from the use of the trans-illuminating cuff of FIG. 1A and the trans-illuminating patch of FIG. 7 with a biological member, such as the arm or head of a neonate.

Illustrated in FIG. 12A is a graphical representation of exemplary signals 700a, 700b (referred to for the remainder of the discussion as a pulse waveform signals) generated by the photodetectors. Pulse waveform signal 700a is obtained after securing the first sensor assembly around limb 200 and energizing the light source and the photodetector. A similar pulse waveform 700b is obtained after securing the second sensor assembly to head 450 and energizing the light source and the photodetector. The rhythmic pattern of fluctuations or oscillations within pulse waveform signals 700a, 700b represent changes in the volumetric flow of blood through limb 200 or head 450 primarily due to the pumping or "beating" action of the human heart.

Subsequent analysis of pulse waveform signals 700a, 700b permit the determination of certain blood parameters that influence the flow of blood, such as, for example, mean arterial blood pressure, diastolic blood pressure and systolic blood pressure. This determination is possible due to the relationships, as discussed above, between transmittance (T) of the optical signal and between reflectance (R) of the optical signal, volumetric changes in blood flow, and blood pressure levels. In an embodiment of the present invention, analysis of pulse waveform signals 700a, 700b includes the application of one or more algorithms that manipulate the data of pulse waveform signals 700a, 700b in accordance with one or more predefined relationships that exist between transmittance (T) and reflectance (R) of the optical signal, blood flow and blood pressure levels. This is further discussed below.

Figure 12B:
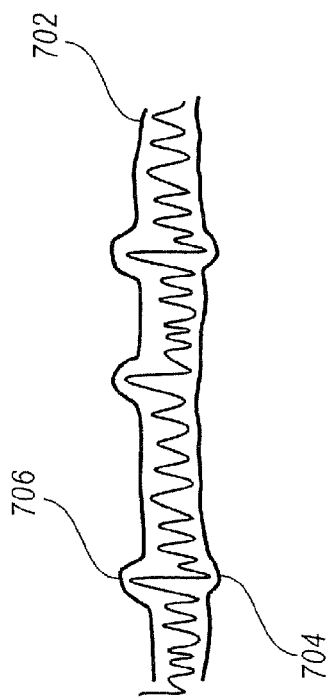
FIGS. 12B-12D are exemplary pulse waveform signals of FIG. 12A that have been positioned within an analysis envelope.
Figure 12C:
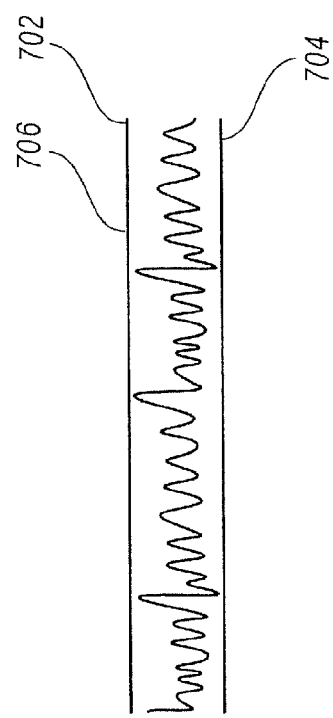
Figure 12D:
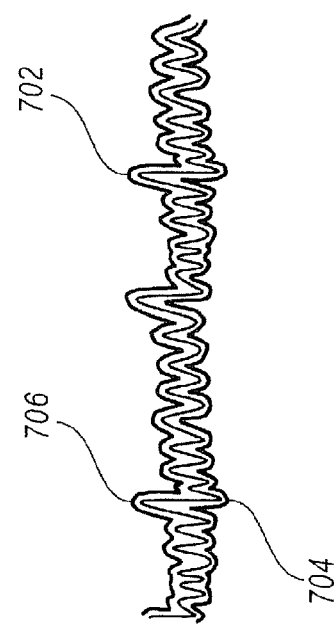

Now referring to FIGS. 12B-12D, the microprocessor may be suitably programmed to generate an envelope 702 from the pulse waveform signal. Envelope 702 is comprised of a lower band 704 and upper band 706 that may be positioned around subsequent pulse waveform signals. Envelope 702 may be used to further aid health care professionals in the near continuous monitoring of a neonate's vital sign parameters and for diagnostic analysis.

Microprocessor 605 may generate envelope 702 from pulse waveform signal 700a by using a signal sampling technique that is known in the art of signal processing. As the microprocessor generates a pulse waveform signal based on the electrical signal received from the sensor assembly (e.g., cuff; patch, clip, or other like device) used to monitor the neonates vital sign parameters, the microprocessor may be programmed to "sample" the pulse waveform signal periodically. Sampling the pulse waveform signal produces a second signal that may be similar to the original pulse waveform signal. The number of samples taken and the time period between samples will determine how closely the sampled signal resembles the original pulse waveform signal taken from the cuff, patch or other like device. Once the sample signal has been generated, the microprocessor may be programmed such that lower band 704 and upper band 706 may be developed from the sampled signal, as determined by a healthcare professional, by adjusting the signal gain to produce envelope 702.

For example, FIG. 12B illustrates envelope 702 that is a set of simple limit bars (lower band 704 and upper band 706) that are based on a sampled electrical signal from the sensor assembly. In this instance, microprocessor samples the pulse waveform signal at only a few points to identify the peak value of the pulse waveform signal. The microprocessor then sets the lower and upper bands of the envelope based upon the peak value or as directed by a healthcare professional. In FIG. 12C, envelope 702 more closely resembles the pulse waveform signal that was generated by the microprocessor from the electrical signal received from the sensor assembly. The envelope in FIG. 12C is based on more frequent sampling of the pulse waveform signal than the envelope in FIG. 12B. The envelope in FIG. 12D is based on an even greater frequency of sampling of the pulse waveform signal then the envelope in FIG. 12C so that the lower and upper bands more closely resemble the actual pulse waveform signal.

The sampling period of the microprocessor may be adjusted to be used in the manner determined by the health care professional. The greater the frequency of the sampling period, the greater the number of sampling points generated, and the more the envelope will resemble the actual electrical signal from the sensor assembly. In this manner the health care professional will have greater precision when employing the use of an envelope in a diagnostic analysis or a near continuous monitor mode.

Once lower band 704 and upper band 706 of envelope 702 have been determined, the health care professional my employ envelope 702 for a number of continuous monitoring and diagnostic analysis techniques. For example, an audible alert may be incorporated into control system 600 such that during continuous monitoring of a neonate with sensor assemblies, an alarm may be sounded if the incoming electrical signal crosses either lower band 704 or upper band 706 indicating a unwanted change in vital sign parameters.

Also, after the signal envelopes have been established, pulse waveform signal 700a may be analyzed through a process of comparing signal 700a to a number of previously established pulse waveform signals that have already been associated with one or more known vital sign measurements. Specifically, the present analysis method involves the creation of a database of reference envelopes based on previous pulse waveform signals and corresponding blood flow characteristics associated with the reference signals. Each individual envelope characteristic in the database or, alternatively, a combination of two or more envelope characteristics, is then associated with one or more vital sign measurements, such as, for example, blood pressure respiration, and heart rate. A pulse waveform signal 700a undergoing analysis is evaluated for one or more identifiable and defining characteristics. These defining characteristics in the evaluated pulse waveform signal 700a are compared to the established envelope characteristics maintained in the database. If this comparison meets certain predetermined criteria between the characteristics of the pulse waveform signal 700a being analyzed and the specific reference characteristics stored in the database, it can be assumed that the blood parameters associated with pulse waveform signal 700a are the same as the known blood parameters associated with the selected reference envelopes stored in the database. The known blood parameters corresponding to the monitored waveform signal 700a may then be presented to the healthcare provider, such as on display 620.

Additionally, the envelopes developed from the pulse waveform signals may be generated and stored in databases for an entire population. A generic database of envelopes may be developed that may be based on age, gender, size, or any number of attributes. By employing the use of these databases, health care professionals may be able to establish a base line reading for those people who have not had a medical physical in quite some time. Rather than taking several months or years to establish a baseline, a generic pulse waveform envelope baseline can be drawn from the database based on parameters such as size, age, and gender, and the person's pulse waveform signal monitored against established envelopes. While, every person will still require an individual assessment, irregularities may be identified in advance with the use of the generic database of envelopes that closely correspond to a particular person's size, age, gender, etc.

For those people that do visit their healthcare professional regularly, an individual database of envelopes may be developed for future diagnostic analysis. One example may involve a person who visits his health care professional for regular physicals. Each time the person returns his yearly physical, the healthcare professional can access his previous envelopes to be used in comparison purposes with the new pulse waveform signal that is presently being generated. The healthcare professional may be alerted to potential physiological problems if the new signal passes outside the envelope indicating a change in the person's vital sign parameters. In another example, a person may find himself in an accident where he is unconscious and cannot communicate with onsite health care professionals. Identification information about the victim can be entered into a computer and the onsite professionals can access the victim's database of pulse waveform signal envelopes to identify any of the victim's vital sign parameter abnormalities that may require attention prior to treating the victim. In this manner, people may receive a relatively quick and accurate diagnosis, which in turn leads to quick and more importantly the correct form of treatment.

Physiological markers that may be monitored and measured by these embodiments may include, but are not limited to, glucose levels, lactate, C-reactive protein, cytokines, white blood cell counts, and gene or protein expression in-vivo. These biological markers not only provide insight into the health status, but also address pre-symptomatic activity due to infection, chemical or biological agent exposure.

Microprocessor 605 may also compare pulse waveform signal 700a produced from the first sensor assembly positioned around limb 200 (see e.g., FIGS. 6A and 6B), with pulse waveform signal 700b produced from the second sensor assembly positioned on head 450 (see e.g., FIG. 9). As discussed above, a database of envelope signals may be created for comparison purposes. The health care provider may monitor these waveforms taken from different areas of the subject to diagnosis possible internal biological problems that may be found between the monitoring devices. Also, the two separate sensor assemblies may be used in conjunction with one another for vital sign comparison purposes and analysis of the neonate.

In addition to the embodiments discussed above, the sensor assembly may also be configured to actively measure blood pressure of a subject through an oscillometric-based method. According to this embodiment, the sensor assembly may include at least one inflatable bladder selectively operable to occlude blood flow in limb 200 or head 450 upon inflation to a sufficiently high enough pressure. An illustrative example of this embodiment will now be discussed with reference to FIGS. 13A and 13B, which depicts a pulse waveform signal 710 along with a graph 720 of corresponding sensor assembly pressure. As in the previous embodiments, a pulse waveform signal 710 is obtained by applying the sensor assembly around limb 200 or to head 450 of the subject and then subsequently energizing the light source to transmit an optical signal through the tissue of the limb or the head to the photodetector. When the bladders are in a deflated state, and thus not significantly impeding the flow of blood through limb 200 or head 450, the sensor assembly will generate a first pulse waveform signal 710a that is similar in nature to the pulse waveform signals 700a, 700b obtained in the previously discussed embodiment of the invention.

Figure 13A:
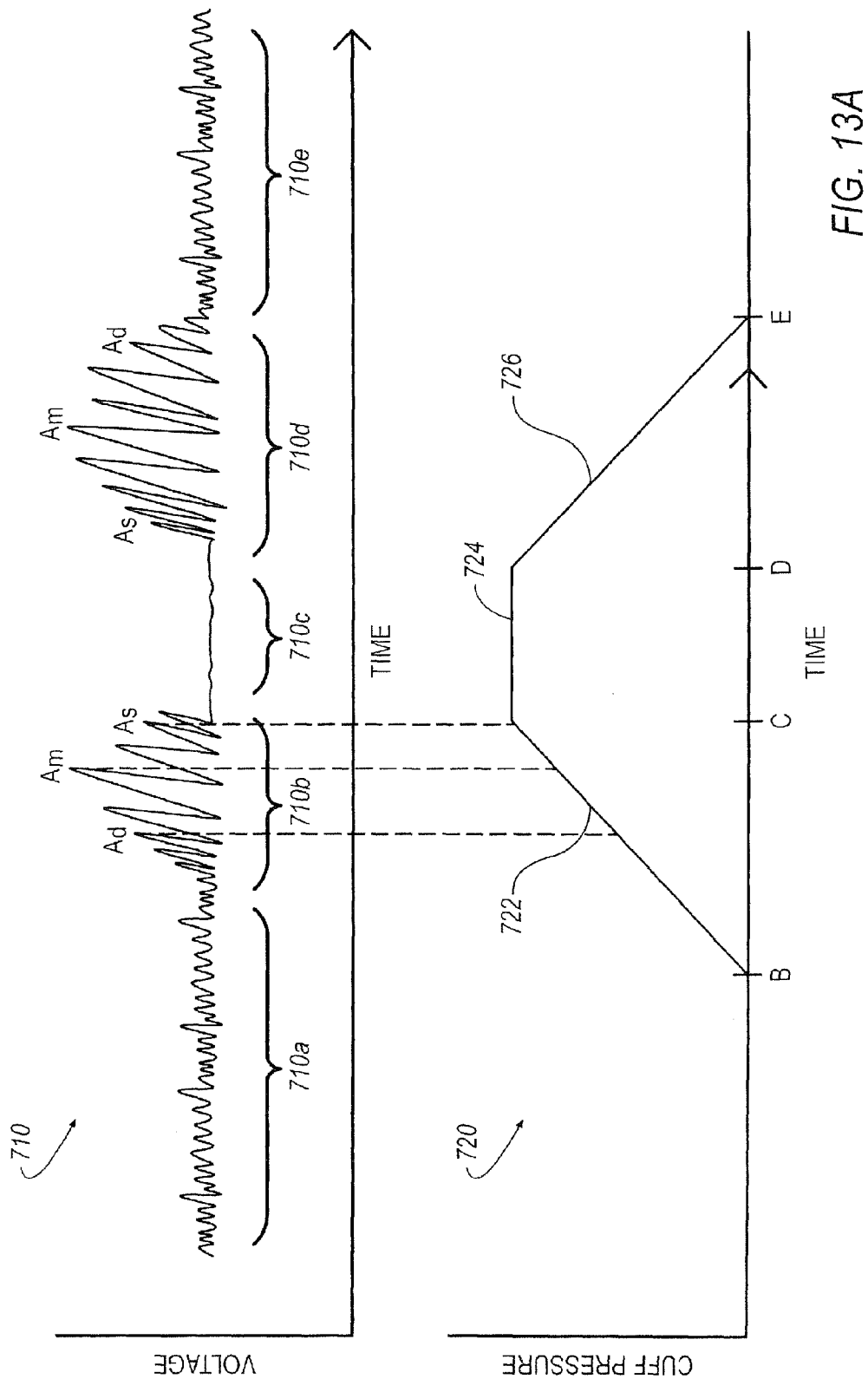
FIGS. 13A and 13B are further exemplary pulse waveform signals illustrating optical oscillometric blood pressure measurements with a vital sign monitor.
Figure 13B:
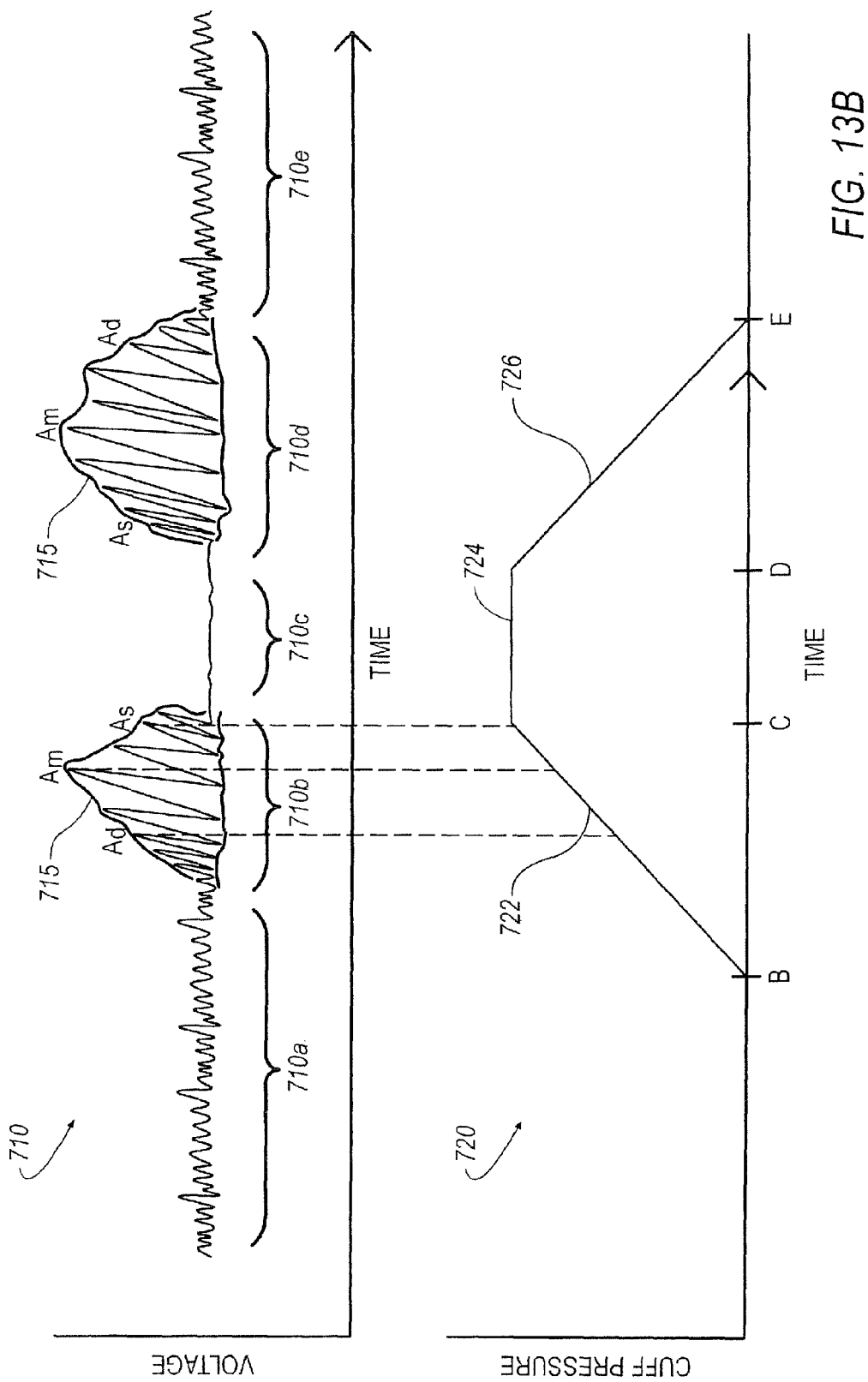

At time B, pump 630a, 630b (illustrated in FIG. 11) activates, thereby increasing the pressure in the bladders, as illustrated in FIGS. 13A and 13B by graph segment 722. As the bladder pressure increases, sensor assembly begins to constrict limb 200 or head 450. This constriction causes at least a partial pinching of the blood vessels running through the limb or the head, which, in turn, impedes blood flow through the blood vessels. During this stage of increasing bladder pressure, the pulses or oscillations in the pulse waveform signal 710b first increase in amplitude, reach a maximum, and then decrease in amplitude. Once the pressure in the bladder exceeds the systolic blood pressure, substantially all blood flow through the limb or head is terminated. The essential lack of blood flow through limb 200 or head 450 during this time period results in a near constant level of transmittance (T) of the optical signal traveling through the tissue of limb 200 or reflectance (R) of the optical signal traveling through the tissue of head 450. As a result of this near constant transmittance (T) or reflectance (R), the pulse waveform signal becomes nearly constant (see, e.g., segment 710c), exhibiting substantially no variances or oscillations in form. At time D, the bladder is allowed to deflate or depressurize at a predetermined rate, as indicated by graph segment 726. The transition period DE in bladder pressure results in amplified oscillations or spikes in the pulse waveform signal (see, e.g., segment 710d). As the sensor assembly returns to an un-pressurized state, the oscillations in the pulse waveform signal (see, e.g., segment 710e) return to a substantially uniform level.

During both transient pressure stages, indicated in FIG. 13B as stages 722 and 726, respectively, the pulse waveform signal exhibits transient increases in the amplitude of the oscillations occurring in the signal (see, e.g., segments 710b and 710d). While the pressure is being increased and decreased by the microprocessor, the microprocessor is also sampling the incoming signal so that an envelope 715 may be generated based upon the transient signal. The positive peak of the envelope is at a point where the pulse amplitude reaches a maximum, identified as mean arterial blood pressure ($A_m$) in FIGS. 13A and 13B. The maximum amplitude of the pulse is also a point where the bladder pressure is substantially equal to mean arterial blood pressure. Similarly, there exist points in waveform signal segments 710b and 710d that correspond to diastolic blood pressure and systolic blood pressure. The determination of the oscillation amplitudes at these points allows for the determination of diastolic and systolic blood pressure. Empirical studies indicate that these oscillation amplitudes, identified as $A_d$ for diastolic pressure and $A_s$ for systolic pressure, are related to the oscillation amplitude $A_m$, which corresponds to mean arterial blood pressure. As such, diastolic blood pressure can be identified by first determining the relationship between $A_d$ and $A_m$, which is a fixed constant, and then determining oscillation amplitude $A_m$, which is readily identifiable since, by definition, it is the oscillation of maximum amplitude. Systolic blood pressure can be identified in a similar manner.

To illustrate the process described above, consider an example where it is assumed that the relationships between the oscillation amplitudes $A_m$, $A_d$, and $A_s$ may be mathematically represented by the equations:

$$A_d/A_m = X, \text{ and}$$

$$A_s/A_m = Y,$$

where X and Y are constants that are empirically determined based on certain characteristics of the subject, such as shape. Upon determination of oscillation amplitude $A_m$ through analysis of the pulse waveform signal, one can readily obtain oscillation amplitudes $A_d$ and $A_s$. The points on the pulse waveform signal that correspond to oscillation amplitudes $A_d$ and $A_s$ are then identified, by interpolation if necessary. The relationship of $A_d/A_m$ is a fixed constant value while the relationship of $A_s/A_m$ may determined by a linear algorithm. Once these points in time are identified, the corresponding cuff pressures that exist at these two times and which correspond, respectively, to diastolic and systolic blood pressures, are readily determined.

After a blood pressure has been determined through the use of the above algorithm, the steady state signal occurring after the deflation of the bladder will have the characteristics of the calculated blood pressure. The steady state signal (e.g. graph segment 710e) generated by the sensor assembly after the measurement of mean arterial pressure and deflation of the bladder, may be monitored in a near-continuous manner. The steady state signal generated after the deflation of the bladder is a signature of the measured mean arterial pressure and the calculated blood pressure. Rather than continuously monitoring blood pressure by inflating and deflating the bladder and disturbing the neonate, an envelope may be positioned around waveform signal 710e and then monitored for one or more predetermined signal characteristics, such as any substantial deviations or fluctuations occurring in the electrical signal that may cross either the lower or upper limit bands of the envelope and indicated an abnormal condition in the neonate. Provided pulse waveform signal 710e remains in a steady state or near steady state condition, it may be assumed that the previously measured blood pressures levels correlating to the waveform signals 710c have not substantially changed. If at any time the generated signal from the sensor assembly passes outside of the envelope, control system 600 may be programmed to trigger an alarm to notify health care professionals of the irregularity and/or perform a new blood pressure measurement and calculation as described above.

In this manner, an actual blood pressure measurement involving inflation of the bladder and subsequent analysis of the pulse waveform signal 710 occurs only when changes in the waveform signal 710e indicate probable changes in blood pressure. In this way, continuous monitoring of blood pressure can be maintained without having the intrusive inflating and deflating of the bladder that may disturb the subject.

In addition to monitoring blood pressure, the sensor assembly may also provide near-continuous monitoring of the pulse or heart rate of the subject. This is accomplished in a manner similar to that previously discussed for providing near-continuous monitoring of blood pressures. Specifically, the sensor assembly is applied to a limb of the subject. If the sensor assembly includes one or more bladders, they should be deflated so as to not constrict the limb, and, consequently, impede blood flow. The light source and the photodetector are energized, generating a pulse waveform signal such as that illustrated in FIG. 12. A similar waveform signal may be generated by a sensor assembly located elsewhere on the subject such as the head. As previously discussed, the pulse waveform signals 700a, 700b are indicative of the volumetric changes Occurring in the flow of blood through the limb or head. A typical pulse waveform signal 700 will be characterized by a rhythmic pattern of fluctuations or oscillations in the signal. These oscillations represent near-continuous changes in the volumetric blood flow due to the pumping or "beating" action of the heart or cardiac muscle. Consequently, heart rate can be monitored by analyzing the waveform signal and determining the number of oscillations that occur within a predetermined period of time.

One primary function of blood is to transport oxygen to all tissues that make up the human body. The ability of blood to "carry" oxygen is due to the presence of hemoglobin (Hb) in the red blood cells. Oxygen brought in by the lungs temporarily binds to the hemoglobin (Hb). The oxygenated hemoglobin (HbO2) is then transported through the circulatory system, where it releases the oxygen to the cells that need it. Through use of a device known as a pulse oximeter, the oxygen saturation level, defined as the ratio of oxygenated hemoglobin (HbO2) to the total amount of hemoglobin (Hb+ HbO2), can be measured and used to help assess the health of an individual.

In an embodiment of the invention, control system 600 may be configured to function as a pulse oximeter. In an embodiment, the sensor assembly, may be configured to generate light of two different wavelengths, such as, for example, 650 nanometers (nm) and 805 nm. As illustrated in FIG. 14, hemoglobin (Hb) offers negligible transmission of light having a wavelength of 650 nm, while oxygenated hemoglobin (HbO2) readily allows for the transmission of light of 650 nm. In contrast, light having a wavelength of 805 nm transmits equally well though both hemoglobin (Hb) and oxygenated hemoglobin (HbO2). Accordingly, the transmission of light at 650 nm indicates a density of oxygenated hemoglobin (HbO2), while the transmission of light at 805 nm indicates a density of total hemoglobin (Hb+HbO2).

To measure blood oxygen saturation levels, control unit 600 may be configured to alternately energize the two light sources of the sensor assembly in rapid succession, e.g., energizing the light sources at 200 pulses per second. In this manner, high-intensity, short duration pulses of first and second wavelengths of light are alternately transmitted through the tissue of limb 200 or head 450. After passing through the tissue of limb 200 or reflecting through the tissue of head 450, the alternating streams of light are received by the photodetectors, which, according to this embodiment, is a broadband photodetector capable of detecting both wavelengths. Alternatively, two separate narrow band photodetectors can be used with the sensor assembly, each photodetector capable of detecting light of one wavelength but not light of the other wavelength. The photodetectors convert the two alternating optical signals of different wavelengths into an electric signal representing the transmittance of two wavelengths. Processor 605 then analyzes the signal and determines the optical density for each of the two wavelengths. The ratio of first wavelength to second wavelength optical density is subsequently calculated and scaled to provide an output value corresponding to the percentage of oxygen saturation. As part of this process, the output value generated from the ratio of optical densities can be compared to an appropriate calibration curve programmed into processor 605, such as, for example, in the form of a lookup table. The calibration curve relates optical density to a suspension, such as blood, and is derived from a variation of Beer's law that relates optical density to the concentration of a dissolved substance.

It may be advantageous to establish a baseline measurement of the transmittance of the two wavelengths of light before using the sensor assembly to measure blood oxygen saturation levels. In an embodiment of the invention, such a baseline measurement may be readily established if the sensor assembly includes at least one inflatable bladder. Specifically, the bladder may be inflated to a sufficiently high enough pressure so that it constricts the limb or head and drives or squeezes substantially all the blood out of the vessels that run within the portion of the limb or head located in the cuff or beneath the patch. The constriction of the limb or head ensures a lack of blood within the optical path established between the light source and the photodetector. An optical signal passed through these bloodless regions of the limb and head can then be assigned a 100% transmission value.

To decrease the sensitivity of the sensor assembly systems to stray ambient light, the photodetectors can be synchronously energized with the light sources. This feature ensures that the photodetectors are turned on only when a light source is energized, and minimizes the amount of power drawn by the system, as well as the amount of heat generated by the light sources and photodetectors.

Figure 15:
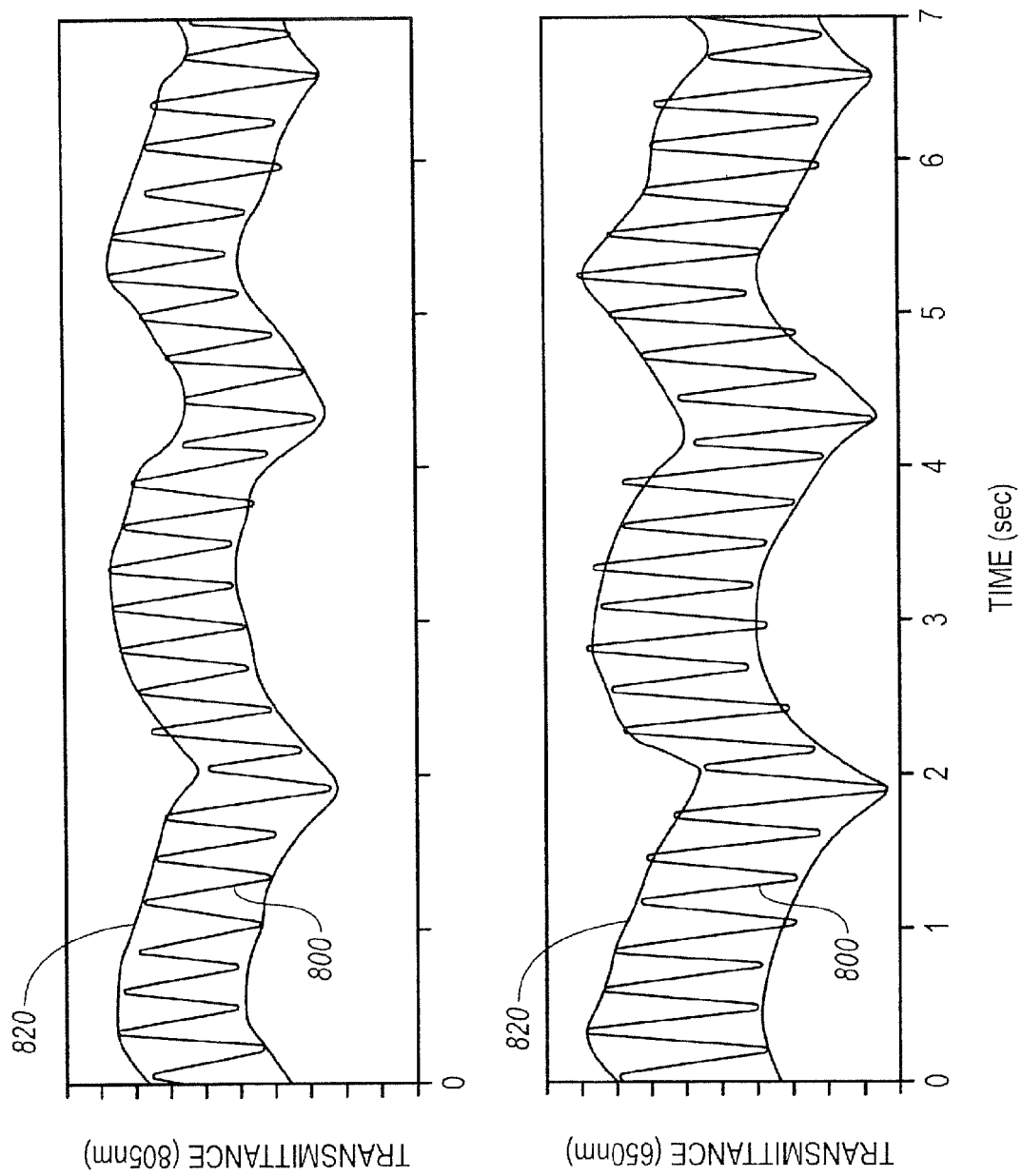
FIG. 15 illustrates the presence of respiratory variations in the graphs of transmittance of light of first and second wavelengths.

The present invention may also be configured to monitor the respiration rate of a neonate. Specifically, blood oxygen saturation levels vary subtly with the breathing process, which includes the inspiration of oxygen and expiration of waste gases such as carbon dioxide. Unlike current commercially available pulse oximeters, the sensor assembly possesses short enough response times in its measuring capabilities to detect the subtle rhythmic changes that occur in blood oxygen saturation levels due to the breathing process. An example of this is illustrated in FIG. 15, which depicts an analog recording of the transmittance of the first and second wavelengths of light, such as 650 nm and 805 nm, used to measure blood oxygen saturation levels. Beyond the relatively high-frequency oscillations 800 that occur in the signals due to the pumping of the cardiac or heart muscle, the more subtle rhythmic variations caused by respiration are readily identified within the signals by the addition of a signal envelope 820.

Figure 16A:
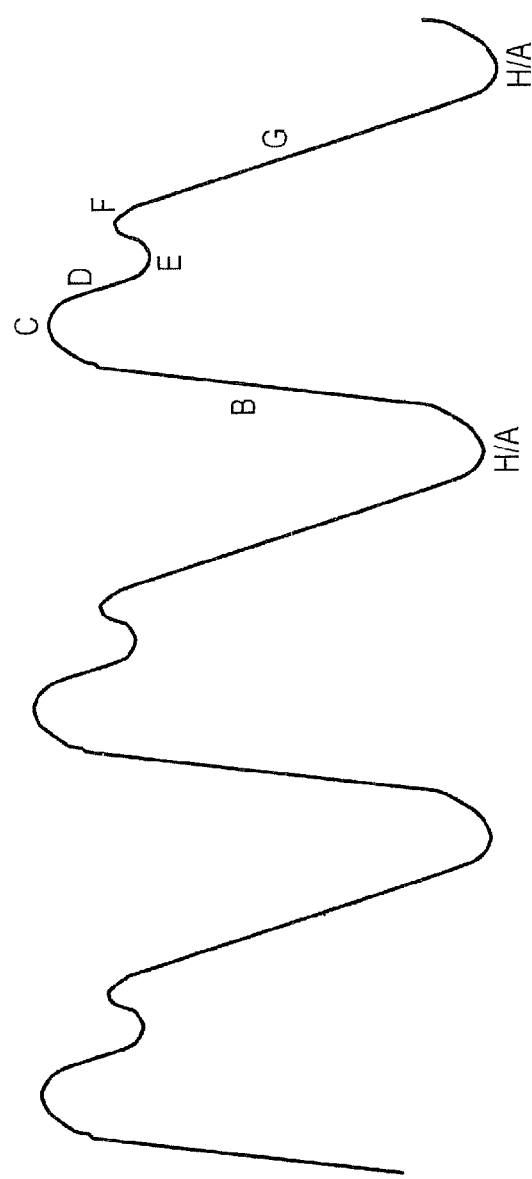
FIGS. 16A and 16B is an exemplary pulse waveform signal that has been labeled to define areas of interest that are related to the pumping action of a heart.
Figure 16B:
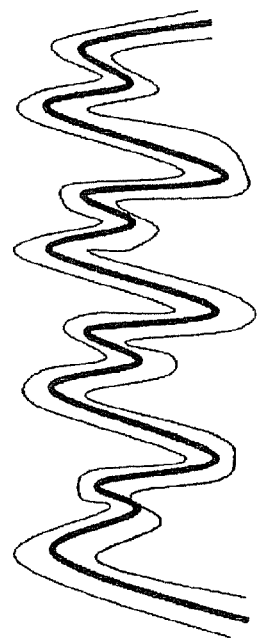

In another embodiment of the present invention, the pulse waveform signal generated by sensor assembly (e.g., cuff 100 or patch 400) may be analyzed to interpret the performance of the cardiovascular and pulmonary systems in a human being. FIGS. 16A and 16B illustrate a pulse volume waveform signal similar to pulse waveform signal 700a of FIG. 12A. The pulse volume waveform signal of FIG. 16A has been labeled as follows to define areas of interest that are related to the pumping action of the heart:

A. Ventricular Contraction
    B. Ventricular Pressure Rises and Ventricular Volume Increases otherwise known as the QRS Complex
    C. Mien ventricular pressure exceeds aortic pressure, the aortic valve opens and blood is ejected into the aorta
    D. Isovolumetric Relaxation, muscle relaxes, but maintains volume, and pressure reduces
    E. The rate of volumetric change is shown by the slope of the curve
    F. Dicrotic Notch is observed and is caused by the closure of the aortic valve
    G. T-Wave (EKG) ends, ventricular pressure decreases, and volume increases
    H., I., J. Are the result of Ventricular Systole
    K., L. Relaxation of the Atrial Chamber provides this signal Changes in A., B., and C. are understood to be related to the capacity of the heart to contract or "pump performance" while changes in E., F., G., and H. are understood to be related to vascular elasticity. The sampling and envelope technique described above in a previous embodiment may be employed to identify changes in the cardio-vascular and pulmonary systems of a particular human being as illustrated in FIG. 16B. The changes in the pulse volume waveform with respect to the envelope may be analyzed and interpreted by a health care professional to predict in advance heart disease and other cardio-vascular events that may be related to a heart attack.

In yet another embodiment of the present invention, the pulse waveform signal generated by the sensor assembly, may be used to produce a Myocardial Contractility Index or "Cardiac Index" and a Tissue Perfusion Index. Myocardial Contractility is the ability of the cardiac muscle to contract. The greater the ability of the cardiac muscle to contract, the greater the cardiac output Tissue perfusion is related to the volume and flow of blood through the blood vessels. Tissue perfusion is related to ability of body tissues to efficiently exchange waste and nutrients with the blood and is related to the oxygen saturation levels. A cardiac index and a perfusion index may be developed from the pulse waveform signals generated by the sensor assembly.

Figure 17:
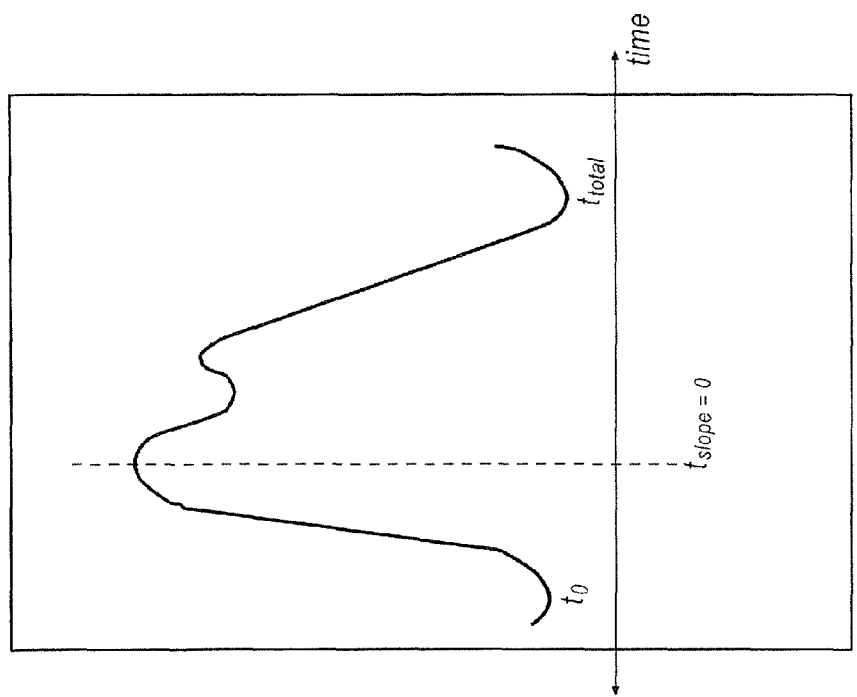
FIG. 17 is an enlarged exemplary pulse waveform signal of FIG. 12A to illustrate transition points of the signal.

FIG. 17 illustrates a pulse volume waveform signal similar to pulse waveform signal 700a of FIG. 12A. The microprocessor may be suitably programmed to determine the slope of the curve as well as the area under the curve associated with a single contraction or beat of the heart. This single contraction is represented by a time period from $t_0$ to $t_{total}$. The maximum acceleration, determined by the upward slope of the curve represents the maximum contractility of the myocardium at a particular heart rate. The change in the slope can be used to develop the Myocardial Contractility Index. Also identified during the single contraction is a point on the curve where the slope of the curve is equal to zero, or $t_{slope=0}$. The Tissue Perfusion Index may be represented by the following ratio in determining the area under the curve to the left of $t_{slope=0}$:

$$\frac{t_0 - t_{slope=0}}{t_0 - t_{total}}$$

As the heart rate increases or decreases, each of the above ratios may change and the rate of change may correlate to underlying heart disease. A small change in heart rate may cause a drastic change in the amount of oxygen being carried in the blood, which changes the efficiency of body tissues to exchange waste and nutrients with the blood.

A Vascular Elasticity Index may also be developed from the same curve used to define the Myocardial Contractility Index and the Tissue Perfusion Index. The Vascular Elasticity Index may be represented by the following ratio in determining the area under the curve to the right of $t_{slope=0}$:

$$\frac{t_{slope=0} - t_{total}}{t_0 - t_{total}}$$

Vascular elasticity is a measure of the flexibility of blood vessels. As the flexibility of the blood vessels increase or decrease, each of the above ratios may change and the rate of change may correlate to an underling constriction of the blood vessels leading to heart disease.

Figure 18A:
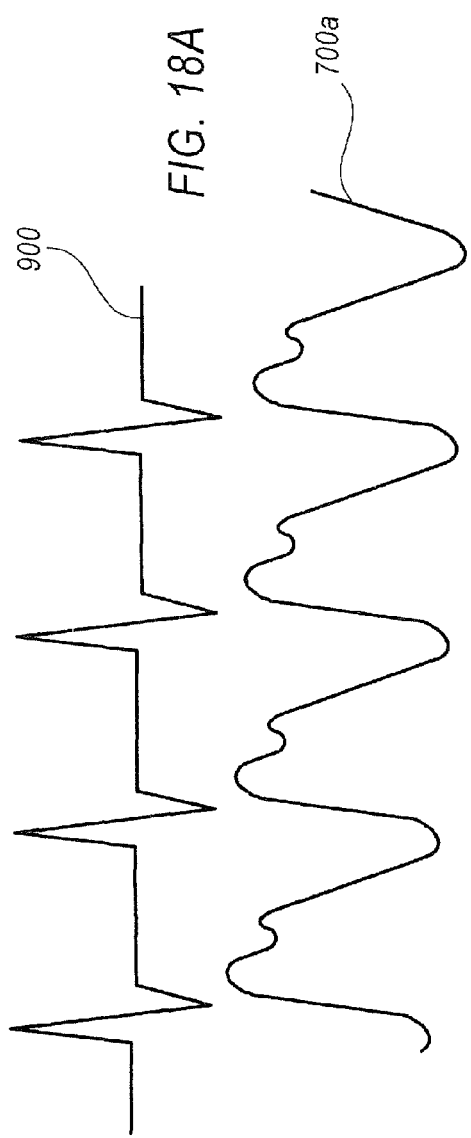
FIGS. 18A and 18B are exemplary electrocardiogram signals and an exemplary pulse waveform signals shown for comparison purposes.
Figure 18B:
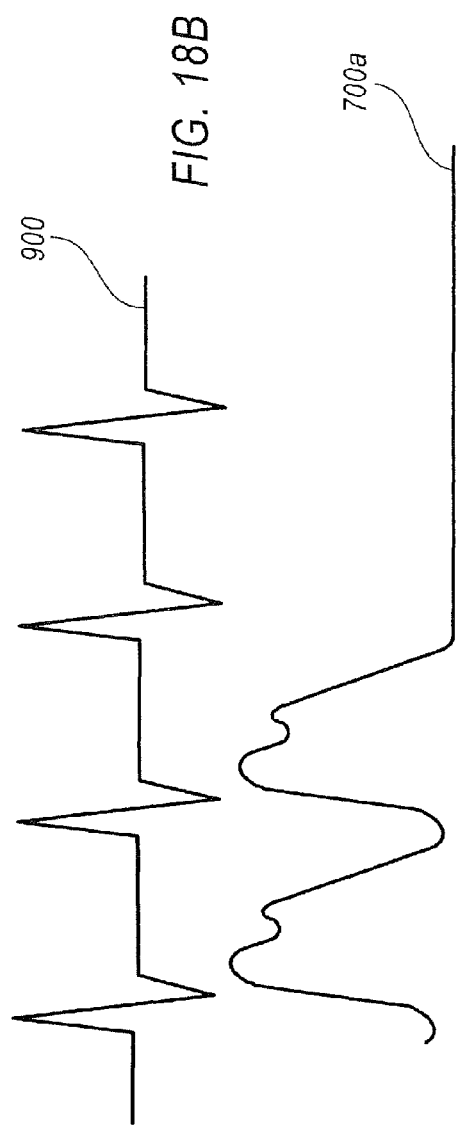

In another embodiment of the present invention, the pulse waveform signal generated from the sensor assembly may be compared to a signal generated from an electrocardiogram (EKG). A traditional EKG is a measurement of the electrical activity of the heart. There may be cases where an EKG may be reflect the normal electrical activity of the heart, yet there is no actual pumping of blood from the heart. This is known in the art as electromechanical disassociation. In this particular embodiment, a sensor assembly, such as patch 400 or cuff 100, may be attached to the skin or implanted within the body near or around a major artery such as the aorta. A signal will be generated by the sensor assembly from the flow of blood through the artery as described in previous embodiments. The signal generated by the sensor assembly measures the actual mechanical pumping of the heart as discussed previously. FIG. 18A illustrates the electrical activity of the heart, an EKG 900, and a signal generated by the pumping action of the heart, the pulse waveform signal similar to 700a. The two signals may be monitored concurrently to identify instances when the electrical activity of the heart, as evidenced by the EKG waveform, is present, yet there is no measurement of tissue perfusion by the sensor assembly, i.e., the heart is not pumping (see FIG. 18B). This would be evidence of electromechanical disassociation. Electromechanical disassociation, if not recognized, may result in death. Also, both signals may be monitored on a particular person that requires the aid of a pacemaker to ensure that the heart is responding to the signals from the pacemaker.

In yet another embodiment of the present invention, a health care professional may rely on the actual measurements of mean arterial pressure (see FIGS. 13A and 13B), myocardial contractility (see FIG. 17), tissue perfusion (see FIG. 17), and vascular elasticity (see FIG. 17) as defined and discussed above to perform a diagnostic analysis or diagnosis of a person without having to rely on a calculation of the traditional diastolic and systolic blood pressure numbers. The measurements described above are all available signals generated from the sensor assemblies that detect the volume and flow of blood through the vessels. A health care professional may rely on the actual measurements rather than the calculated systolic and diastolic blood pressure numbers to provide a more precise and accurate diagnosis of the pulmonary system of any particular person.

Databases of envelopes may also be created as described in previous embodiments based on the above measurements to develop a number diagnostic indexes such as the cardio index, tissue perfusion index, and vascular elasticity index. These databases may be developed either generically across a population of people based on age, gender, size, etc., or specific to one person based on previous physicals and signal monitoring. The above indexes along with a measurement of mean arterial pressure may be used to quickly, precisely, and accurately diagnose a potentially fatal pulmonary issue if left untreated and more importantly undiscovered.

In another embodiment of the present invention, a sensor assembly, such as patch 400 or similar device may be adapted for use in an effort monitor the physical health of a person on the battlefield or in flight during a war or fighting situation. The embodiments described above to generate pulse waveform signals to monitor vital sign parameters may be employed to continuously or periodically monitor a person's physical health in battle. Rather than being connected directly to control system 600 as described in previous embodiments, radio frequency, ultrasonic, or optical based signals may be employed to transmit signals between an individual soldier and a central command center monitoring all soldiers. Low power devices such as patch 400 may be directly interfaced onto the soldier's outer skin or incorporated into their uniforms or gear.

It will be appreciated from the above description the sensor assemblies of the present invention provides significant advantages over prior art systems and methods by providing the ability to monitor blood parameters, such as blood pressure, heart rate, oxygen saturation and respiration rate, in a near-continuous manner through analysis of a single optical signal. Furthermore, the non-invasive features of the present invention make it an ideal blood parameter monitor for use with neonates. Traditional monitoring devices, such as, for example, auscultatory and prior oscillometric-based methods for monitoring blood pressure, are frequently ineffective with subjects such as neonates due to their relatively small size. In contrast, the sensor assemblies of the present invention are capable of accurately monitoring blood parameters in a relatively small biological entity by transmitting an optical signal through the limb or head of the biological entity. Indeed, the smaller the biological entity, the less tissue the optical signal has to traverse, resulting in a stronger signal that is received by the photodetector and subsequently analyzed to determine vital sign parameters such as, for example, blood pressure.

In the foregoing discussion, the present invention has been drawn to a system and method for monitoring certain vital sign parameters of a neonate by directing an optical signal through the tissue of the neonate's limb or forehead. According to the embodiments discussed up until now, this is accomplished through the use of a cuff-based or patch-based structure that wraps around a limb or is position on a head, or, alternatively, into which a limb is inserted, the cuff and patch structure thereby retaining a light source and photodetector in proximity to the limb and head. However, it is envisioned that the present invention can be implemented in numerous other configurations that would be as equally effective in providing near-continuous monitoring of certain blood parameters of a neonate. For example, according to one additional embodiment of the invention, no such type of cuff structure is utilized. Instead, the light source and photodetector are selectively retained in proximity to the limb through the use of some form of clip or clamping structure that does not encircle the entire limb or, alternatively, through the use of a removable adhesive.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A system comprising:
   a processor;
   a sensor in communication with the processor, including:
      at least one light source; and
      at least one photodetector;
   a display in communication with the processor;
   an alarm in communication with the processor; and
   a memory storing instructions executable by the processor for activating the alarm when a sensor response meets at least one predefined criterion;
   the memory further storing instructions for periodically acquiring sensor responses, sampling the sensor responses at a sampling frequency to develop a waveform, developing a reference envelope having a lower limit band and an upper limit band wherein a proximity of the envelope to the waveform is based at least in part on the sampling frequency, and storing the envelope in the memory; and
   wherein the at least one predefined criterion includes the photodetector response crossing the upper or lower limit of the envelope.

2. The system of claim 1, further comprising an electrocardiograph, the memory further storing instructions for acquiring and analyzing signals from the electrocardiograph.

3. The system of claim 2, the memory further storing instructions for comparing the acquired electrocardiograph signals with a sensor response, and identifying a heart condition of electromechanical disassociation by determining when the electrocardiograph signal represents electrical activity in the heart and the sensor response represents the absence of pumping action in the heart.

4. The system of claim 2, the memory further storing instructions for transmitting information from at least one of the sensor and the electrocardiograph to the display, determining at least one characteristic from the information wherein the characteristic is at least one of a blood parameter and a physiological marker, and displaying the characteristic in response to a request.

5. The system of claim 1, the memory further storing a record, wherein the record relates to at least one of a blood parameter and a physiological marker.

6. The system of claim 5, wherein the record is at least one of a previously-acquired record for a biological entity and a record representing a population, wherein the population is categorized by at least one of age, gender, height, weight, race, geographic residence, medical history, medical condition, education, military service, and occupation.

7. The system of claim 5, the memory further storing instructions for developing a set of characteristics from the sensor responses including at least one of a blood parameter and a physiological marker, comparing the set of characteristics to the record, determining a different blood parameter, and displaying at least one of the different blood parameter and a characteristic from the set of characteristics.

8. The system of claim 1, wherein the sensor is configured to be implanted into a biological entity.

9. The system of claim 1, wherein the sampling frequency is user-adjustable.

10. The system of claim 1, wherein the sensor comprises a pulse oximetry sensor for measuring blood oxygen saturation.

11. A method, comprising:
   activating a light source that is included in a sensor positioned proximate a biological entity;
   activating a photodetector that is included in the sensor;
   acquiring a pulse waveform signal from the photodetector corresponding to a blood flow characteristic of the biological entity;
   sampling the pulse waveform signal to obtain a second sampled signal;
   identifying a peak value of the second sampled signal;
   developing a reference envelope with a lower limit band and an upper limit band based at least in part on the peak value and a user input, and activating an alarm when an incoming signal from the photodetector crosses the upper or lower limit of the envelope.

12. The method of claim 11, further comprising periodically acquiring photodetector responses, developing a set of characteristics from the photodetector responses including at least one of a blood parameter and a physiological marker, comparing the set of characteristics to a record, determining a different blood parameter, and displaying at least one of the different blood parameter and a characteristic from the set of characteristics.

13. The method of claim 11, further comprising acquiring signals from an electrocardiograph, comparing the acquired electrocardiograph signals with the incoming signal, and identifying a heart condition of electromechanical disassociation when the electrocardiograph signal represents electrical activity in the heart and the photodetector response represents the absence of pumping action in the heart.

14. The method of claim 11, further comprising acquiring signals from an electrocardiograph, developing a set of characteristics from at least one of the pulse waveform signal and the electrocardiograph signal, and displaying at least one characteristic of the set of characteristics in response to a request.

15. The method of claim 11, wherein sampling the pulse waveform signal comprises sampling at a sampling rate, wherein developing the reference envelope comprises positioning the lower limit band and the upper limit band based at least in part on the sampling rate, and wherein the sampling rate is user-adjustable.

16. The method of claim 11, further comprising generating a database of reference envelope characteristics, and comparing the pulse waveform signal to the reference envelope characteristics in the database.

17. The method of claim 11, wherein the user input comprises a sampling frequency of the sampling of the pulse waveform signal.

18. The method of claim 11, wherein the user input comprises an amount of offset of the envelope.

* * * * *